US005657963A

United States Patent [19]
Hinchliffe et al.

[11] Patent Number: 5,657,963
[45] Date of Patent: Aug. 19, 1997

[54] SEAL ASSEMBLY FOR ACCOMMODATING INTRODUCTION OF SURGICAL INSTRUMENTS

[75] Inventors: Peter W. J. Hinchliffe, New Haven; Robert C. Smith, Danbury; Richard D. Gresham, Monroe, all of Conn.

[73] Assignee: United States Surgical Corporation, Norwalk, Conn.

[21] Appl. No.: 356,436

[22] Filed: Dec. 15, 1994

Related U.S. Application Data

[63] Continuation-in-part of Ser. No. 80,465, Jun. 16, 1993, Pat. No. 5,492,304.

[51] Int. Cl.$^6$ .................................................. F16L 37/28
[52] U.S. Cl. ...................... 251/149.1; 604/167; 604/256
[58] Field of Search .......................... 251/149.1; 604/167, 604/256

[56] References Cited

U.S. PATENT DOCUMENTS

| | | |
|---|---|---|
| 729,423 | 5/1903 | Scheiber et al. . |
| 2,797,837 | 7/1957 | Roberts . |
| 3,086,797 | 4/1963 | Webb . |
| 3,197,173 | 7/1965 | Taubenheim . |
| 3,438,607 | 4/1969 | Williams et al. . |
| 3,766,916 | 10/1973 | Moorehead et al. . |
| 3,811,440 | 5/1974 | Moorehead et al. . |
| 3,856,010 | 12/1974 | Moorehead et al. . |
| 3,875,938 | 4/1975 | Mellor . |
| 3,920,215 | 11/1975 | Knauf . |
| 3,970,089 | 7/1976 | Saice . |
| 3,977,400 | 8/1976 | Moorehead . |
| 3,994,287 | 11/1976 | Turp et al. . |
| 4,000,739 | 1/1977 | Stevens . |
| 4,149,535 | 4/1979 | Volder . |
| 4,177,814 | 12/1979 | Knepshield . |
| 4,231,400 | 11/1980 | Friedling et al. . |
| 4,240,411 | 12/1980 | Hosono . |
| 4,243,034 | 1/1981 | Brandt . |
| 4,324,239 | 4/1982 | Gordon et al. . |
| 4,338,933 | 7/1982 | Bayard et al. ............... 251/149.1 |
| 4,378,013 | 3/1983 | LeFevre . |
| 4,424,833 | 1/1984 | Spector et al. . |
| 4,430,081 | 2/1984 | Timmermans . |
| 4,436,519 | 3/1984 | O'Neil . |
| 4,473,369 | 9/1984 | Lueders et al. . |
| 4,475,548 | 10/1984 | Muto . |
| 4,496,348 | 1/1985 | Genese et al. . |
| 4,580,573 | 4/1986 | Quinn . |
| 4,610,665 | 9/1986 | Matsumoto et al. . |
| 4,610,674 | 9/1986 | Suzuki et al. . |

(List continued on next page.)

FOREIGN PATENT DOCUMENTS

| | | |
|---|---|---|
| 0344907 | 6/1989 | European Pat. Off. . |
| 0350291 | 1/1990 | European Pat. Off. . |
| 0567141 | 10/1993 | European Pat. Off. . |
| 0567142 | 10/1993 | European Pat. Off. . |
| 0630660 | 12/1994 | European Pat. Off. . |
| 2019219 | 10/1979 | United Kingdom . |
| 2065479 | 7/1982 | United Kingdom . |
| 9301850 | 2/1993 | WIPO . |
| WO9417844 | 8/1994 | WIPO . |

*Primary Examiner*—A. Michael Chambers

[57] ABSTRACT

A seal assembly is provided which includes a housing and resilient first seal member associated with the housing. The first seal member is preferably a gasket having an aperture formed therein for receiving surgical instrumentation adapted to cooperate with a dilating means having an exterior face associated with the housing for dilating the aperture of the gasket. The first seal member and the dilating member are adapted for relative movement therebetween, the first seal member and the dilating member assuming a first position wherein the aperture of the first seal member is spaced from the dilating member and assuming a second position wherein the aperture of the first seal member is stretched around the exterior face of the dilating member. A flexible member may also be provided to help maintain a seal between the first seal member and an instrument inserted therethrough, in particular when the instrument is moved in a transverse direction.

28 Claims, 36 Drawing Sheets

U.S. PATENT DOCUMENTS

| | | |
|---|---|---|
| 4,626,245 | 12/1986 | Weinstein . |
| 4,634,421 | 1/1987 | Hegemann . |
| 4,654,030 | 3/1987 | Moll et al. . |
| 4,655,752 | 4/1987 | Honkanen et al. . |
| 4,673,393 | 6/1987 | Suzuki et al. . |
| 4,699,356 | 10/1987 | Hargrove et al. .................... 251/149.1 |
| 4,715,360 | 12/1987 | Akui et al. . |
| 4,723,550 | 2/1988 | Bales et al. . |
| 4,758,225 | 7/1988 | Cox et al. . |
| 4,786,028 | 11/1988 | Hammond . |
| 4,798,594 | 1/1989 | Hillstead . |
| 4,817,631 | 4/1989 | Schnepp-Pesch et al. . |
| 4,839,471 | 6/1989 | Clark et al. . |
| 4,842,591 | 6/1989 | Luther . |
| 4,857,062 | 8/1989 | Russell . |
| 4,869,717 | 9/1989 | Adair . |
| 4,895,346 | 1/1990 | Steigerwald . |
| 4,895,565 | 1/1990 | Hillstead . |
| 4,909,798 | 3/1990 | Fleischhacker et al. . |
| 4,917,668 | 4/1990 | Handl . |
| 4,929,235 | 5/1990 | Merry et al. . |
| 4,960,259 | 10/1990 | Sunnanväder et al. . |
| 4,960,412 | 10/1990 | Fink . |
| 4,966,588 | 10/1990 | Rayman et al. . |
| 4,978,341 | 12/1990 | Niederhauser . |
| 5,000,745 | 3/1991 | Guest et al. . |
| 5,009,391 | 4/1991 | Steigerwald . |
| 5,009,643 | 4/1991 | Reich et al. . |
| 5,041,095 | 8/1991 | Littrell . |
| 5,053,014 | 10/1991 | Van Heugten . |
| 5,053,016 | 10/1991 | Lander . |
| 5,064,416 | 11/1991 | Newgard et al. . |
| 5,069,424 | 12/1991 | Dennany, Jr. et al. .............. 251/149.1 |
| 5,104,383 | 4/1992 | Shichman . |
| 5,104,389 | 4/1992 | Deem et al. . |
| 5,127,626 | 7/1992 | Hilal et al. . |
| 5,127,909 | 7/1992 | Shichman . |
| 5,167,636 | 12/1992 | Clement . |
| 5,180,373 | 1/1993 | Green et al. . |
| 5,195,980 | 3/1993 | Catlin . |
| 5,197,955 | 3/1993 | Stephens et al. . |
| 5,209,737 | 5/1993 | Ritchart et al. . |
| 5,226,891 | 7/1993 | Bushatz et al. . |
| 5,269,771 | 12/1993 | Thomas et al. ..................... 251/149.1 |
| 5,308,336 | 5/1994 | Hart et al. . |
| 5,342,315 | 8/1994 | Rowe et al. . |
| 5,385,553 | 1/1995 | Hart et al. . |
| 5,411,483 | 5/1995 | Loomas et al. . |
| 5,423,848 | 6/1995 | Washizuka et al. . |
| 5,476,475 | 12/1995 | Gadberry . |
| 5,492,304 | 2/1996 | Smith et al. . |

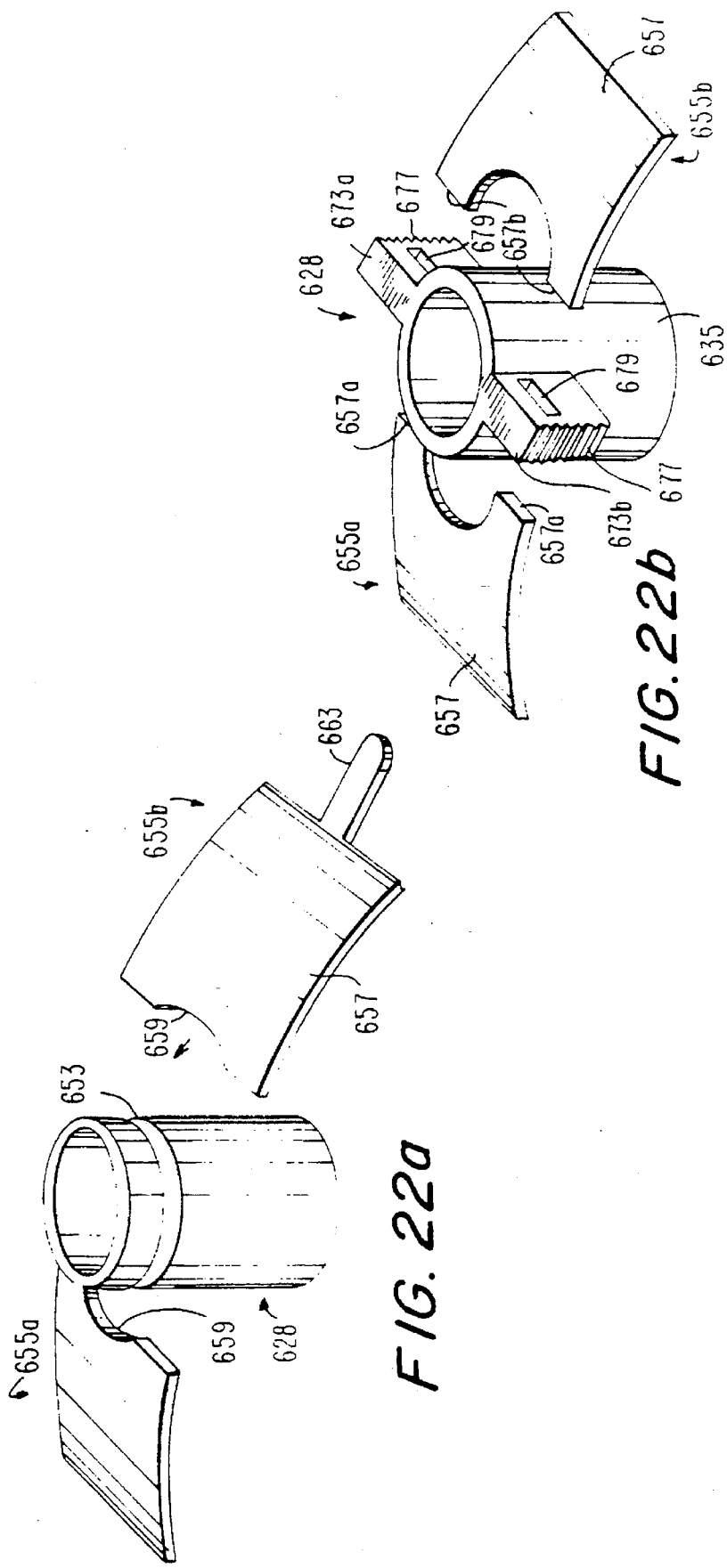

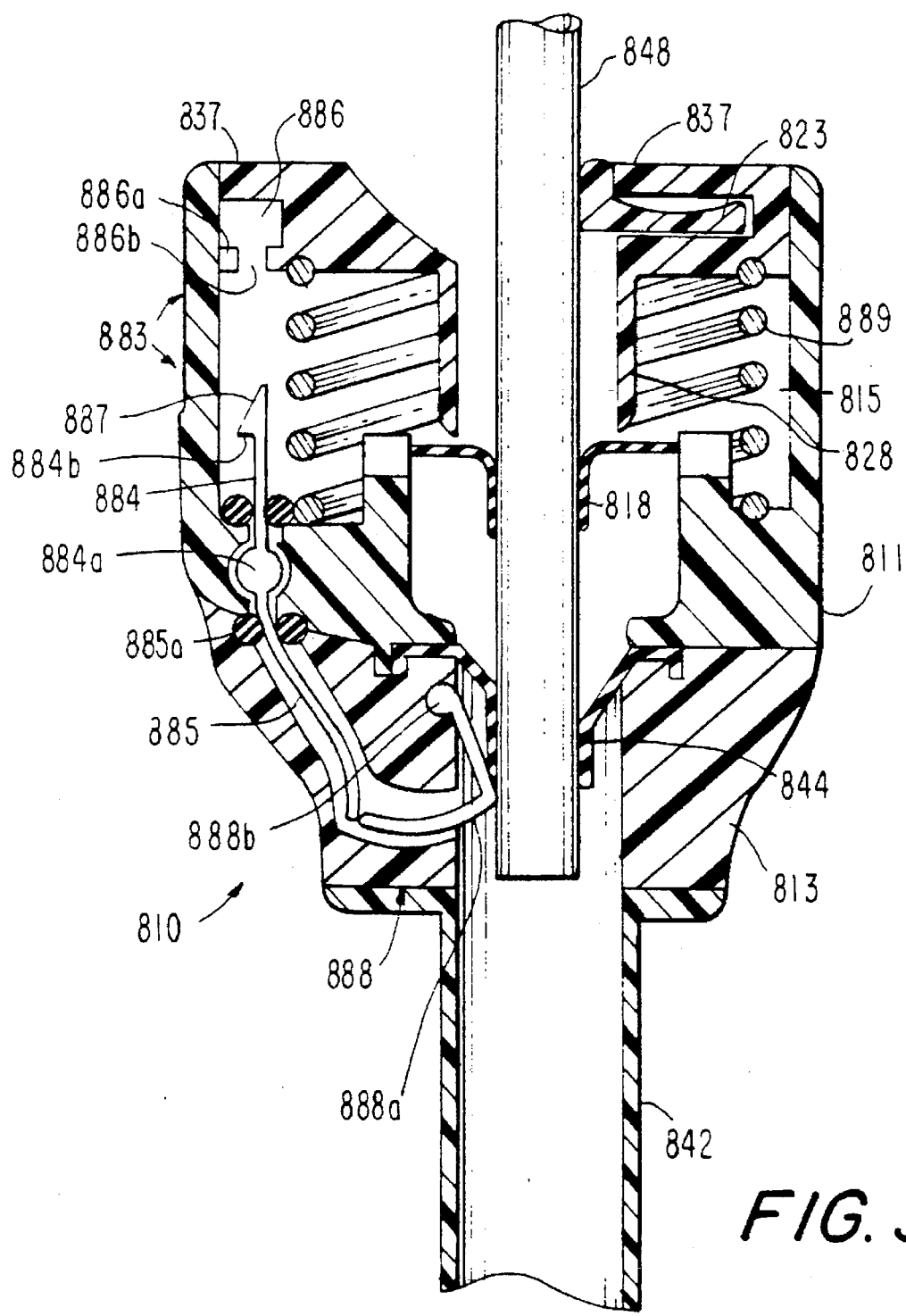

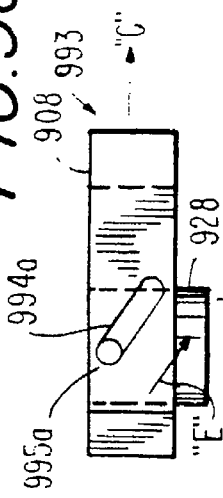
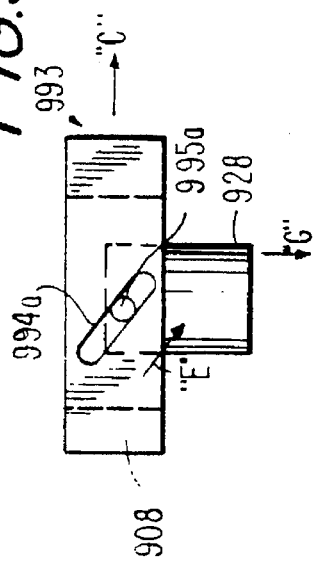
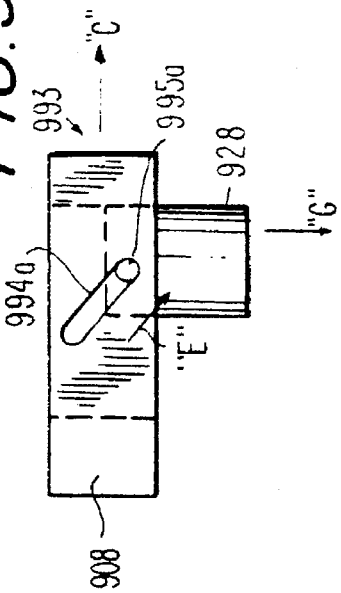
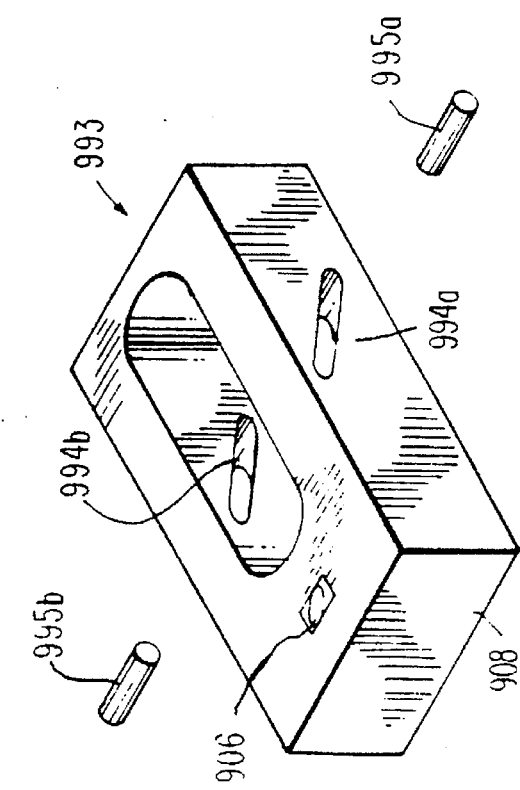
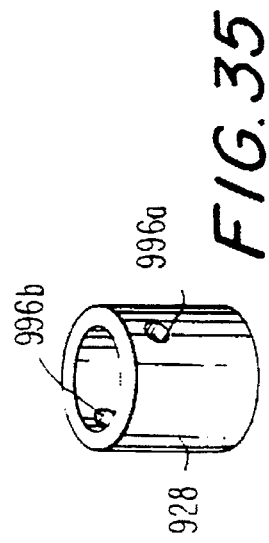

SEAL ASSEMBLY FOR ACCOMMODATING INTRODUCTION OF SURGICAL INSTRUMENTS

This application is a continuation-in-part of U.S. patent application Ser. No. 08/080,465 filed on Jun. 16, 1993, now U.S. Pat. No. 5,492,304, issued on Feb. 20, 1996.

BACKGROUND

1. Technical Field

This application relates to seal systems which are adapted to allow the introduction of surgical instrumentation into a patient's body. In particular, the seal system is applicable to a cannula assembly wherein a cannula housing includes or is adapted to receive a seal assembly to sealingly accommodate instruments of different diameters inserted through the seal assembly and cannula.

2. Background of the Related Art

In laparoscopic procedures surgery is performed in the interior of the abdomen through a small incision; in endoscopic procedures surgery is performed in any hollow viscus of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly comprised of a cannula assembly and an obturator assembly. Since the cannula assembly provides a direct passage for surgical instrumentation from outside the patient's body to access internal organs and tissue, it is important that the cannula assembly maintain a relatively gas-tight interface between the abdominal cavity and the outside atmosphere. The cannula assembly thus generally includes a cannula attached to a cannula housing containing a seal assembly adapted to maintain a seal across the opening of the cannula housing.

Since minimally invasive surgical procedures in the abdominal cavity of the body generally utilize insufflating gases to raise the cavity wall away from vital organs, the procedure is usually initiated by use of a Verres needle through which a gas such as $CO_2$ is introduced into the body cavity, thereby creating a pneumoperitoneum. Thereafter, the pointed obturator of the obturator assembly is inserted into the cannula assembly and used to puncture the abdominal wall. The gas provides a positive pressure which raises the inner body wall away from internal organs, thereby providing the surgeon with a region within which to operate and avoiding unnecessary contact with the organs by the instruments inserted through the cannula assembly. Following removal of the obturator assembly from the cannula assembly, laparoscopic or endoscopic surgical instruments may be inserted through the cannula assembly to perform surgery within the abdominal cavity.

Without the obturator assembly to block the flow of insufflation gas out from the cavity, other structure must be provided to maintain a relatively fluid-tight interface between the abdominal cavity and the outside atmosphere. Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula. Additionally, as endoscopic and laparoscopic surgical procedures and techniques have advanced, it has become desirable to accommodate surgical instrumentation of varying outside diameters through a single cannula assembly in a given surgical procedure, thereby minimizing the number of cannulae required and facilitating efficiency in the surgical procedure.

Various seal systems have been provided for maintaining the pneumoperitoneum in the cavity when no trocar or other surgical instrument is present in the cannula. For example, a pivotally mounted flapper valve may be provided which pivots open upon insertion of an instrument and pivots closed, under a spring bias, once the instrument is removed. Conventional flapper valves may also be manually opened by pivoting a lever provided on the exterior of the housing. An example of such a flapper valve is disclosed in U.S. Pat. No. 4,943,280 to Lander. Trumpet valves are also well known for use in sealing a cannula assembly in the absence of a surgical instrument.

Various seal systems have also been provided for sealing against instrumentation inserted through a cannula. U.S. Pat. No. 4,655,752 to Honkanen et al. discloses a cannula including a housing and first and second seal members. The first seal member is conically tapered towards the bottom of the housing and has a circular opening in its center, while the second seal member is cup-shaped. The second seal member includes at least one slit to allow for passage of instruments.

U.S. Pat. No. 4,929,235 to Merry et al. discloses a self-sealing catheter introducer having a sealing mechanism to prevent blood or fluid leakage that includes a conical sealing element and a planar sealing element having a slit, the planar sealing element being positioned distal of the conical sealing element so that when the distal planar sealing element is moved proximally it rests upon the conical sealing element, each sealing element being adapted to surround a tube.

U.S. Pat. Nos. 4,874,377 and 5,064,416 to Newgard et al. relate to a self-occluding intravascular cannula assembly in which an elastomeric valving member is positioned transversely to a housing and is peripherally compressed to cause displacement, distortion and/or theological flow of the elastomeric material. A frustroconical dilator projection is provided which cooperates with the elastomeric valving member in moving the valving member to a non-occluding position.

U.S. Pat. No. 5,104,3838 to Shichman relates to a trocar adapter seal which is adapted to be associated with a cannula assembly and which advantageously reduces the diameter of the cannula assembly to accommodate instruments of smaller diameter. The trocar adapter seal may be removed from the cannula assembly so that the cannula assembly may once again accommodate instruments of larger diameter. WO 93/04717 to Mueller et al. describes a similar trocar adapter seal system in which a pair of seal adapter plates are slidably mounted to the cannula housing and may be selectively positioned transverse the cannula housing aperture for accommodating surgical instrumentation therethrough.

Cannula assemblies have also been developed which are provided with a series of resilient sealing elements having a central aperture, e.g., commonly assigned, co-pending applications Ser. No. 07/874,291 filed Apr. 24, 1992 and Ser. No. 07/873,416 filed Apr. 24, 1992. Upon insertion of an instrument, the sealing elements resiliently receive the instrument, while maintaining a seal around the instrument across a range of instrument diameters, e.g., 5 to 12 mm. Upon withdrawal of the instrument, a fluid-tight seal is provided by the internal sealing elements.

Although attempts have been made to provide a seal assembly as part of or for use in conjunction with a cannula assembly which maintains the integrity of the seal between the body cavity and the atmosphere outside the patient's body, seal systems provided to date have failed to address the full range of surgeons' needs, especially when it is desired to utilize different instruments having different diameters therethrough.

SUMMARY

A seal assembly is provided which will allow a surgeon to efficaciously utilize instruments of varying diameter in a surgical procedure. The seal assemblies described herein obviate the need for multiple adapters to accommodate instruments of varying diameter by providing a dilating funnel which is adapted to spread open the aperture of a seal member, thereby allowing the seal member to receive larger instrumentation with minimal force required on the part of the user.

More particularly, a seal assembly is provided which includes a housing and a resilient first seal member associated with the housing, the first seal member having an aperture formed therein for receiving surgical instrumentation. The first seal member is preferably a substantially planar, resilient gasket that is mounted transverse with respect to the housing. The seal assembly further includes a dilating member associated with the housing for dilating the aperture of the first seal member. In one embodiment, the first seal member and the dilating member are adapted for relative movement therebetween, such that the first seal member and the dilating member assume a first position wherein the aperture of the first seal member is spaced from the dilating member and is adapted to receive surgical instrumentation of a first diameter with minimal insertion force, i.e., less than about 2 lbs. and preferably less than about 1 lb., and assume a second position wherein the aperture of the first seal member is stretched around the exterior face of the dilating member for receiving surgical instrumentation of a second diameter greater than the first diameter with minimal insertion force, i.e., less than about 2 lbs. and preferably less than about 1 lb.

In a second embodiment, the first seal member and the dilating member are also adapted for relative movement therebetween, but when the dilating member assumes the first position spaced from the first seal member no instrumentation may be received through the first seal member. The dilating member assumes a second position wherein the first seal member is stretched around the exterior face of the dilating member for receiving surgical instrumentation of varying diameter with minimal insertion force, i.e., less than about 2 lbs. and preferably less than about 1 lb.

Preferably, the housing of the seal assembly is adapted to be detachably associated with a cannula assembly which includes a cannula housing and a tubular cannula. Alternatively, the seal assembly may be mounted to the cannula assembly. In either case, the cannula assembly preferably includes a second seal member positioned within the cannula housing, such second seal member preferably comprising a distally directed duckbill member. The second seal member preferably provides a substantially fluid-tight seal in the absence of a surgical instrument passed therethrough. This substantial fluid-tight seal need only be provided, however, when the cannula assembly is introduced to an insufflated body cavity, in which case the positive pressure within the body cavity may force the distal faces of the preferred duckbill member into sealing abutment with each other. If the housing of the seal assembly is detachably associated with the cannula assembly, then a third, substantially planar gasket is preferably provided. The third seal member is preferably a substantially planar, resilient gasket that is mounted transverse with respect to the cannula housing, the aperture of the third resilient gasket being of larger diameter than the aperture of the second resilient gasket found in the sealing assembly.

The housing of the seal assembly of the first embodiment preferably includes a bellows structure which is adapted to assume an extended position which corresponds to the first position of the first seal member and the dilating member, and a collapsed position which corresponds to the second position of the first seal member and the dilating member. The bellows structure may be encased within a rigid outer frame which defines a constant axial dimension for the seal assembly or, in the absence of such outer frame, movement of the bellows structure to the collapsed position may reduce the overall axial dimension of the seal assembly. The seal assembly may further comprise a flange associated with the bellows structure for moving the bellows structure between the extended position and the collapsed position. A biasing member, e.g., a spring, may be provided for biasing the bellows structure to the extended position. Alternatively, the resilience of the material from which the bellows structure and/or the first sealing member are fabricated may serve to bias the bellows structure to the extended position. A vent may also be provided between the interior of the bellows structure and the dilating member such that air within the bellows structure has a path of egress when the bellows structure is collapsed. To prevent unacceptable gas leakage from the insufflated body cavity when such vent is provided, the bellows structure preferably cooperates with adjoining structures to define a substantially fluid-tight region, with the exception of the vent described above.

Alternatively, the housing of the seal assembly may comprise a rigid outer frame having a flexible biasing member disposed therein, e.g., a spring disposed within the rigid outer frame. The biasing member assumes a first, substantially stress-free position which corresponds to the first position of the first seal member and the dilating member, and assumes a second position which corresponds to the second position of the first seal member and the dilating member. The flexible nature of the biasing member allows the dilating member and the first seal member to move easily between the first position and the second position, while providing an appropriate bias force toward the first position.

The housing of the seal assembly of one embodiment preferably includes a flexible member disposed within the housing, adjacent the first seal member. The flexible member allows for transverse movement of the first seal member with respect to the housing in order to help maintain a seal between the first seal member and a surgical instrument inserted through the housing, in particular when the instrument is moved in a transverse direction.

As noted above, the cannula assembly may include a third, substantially planar gasket. This gasket is preferably positioned proximal the distally directed duckbill member. In such case, the dilating member may include a proximally directed dilating funnel for spreading the gasket associated with the seal assembly and a distally directed member which is adapted to contact and expand the planar gasket of the second seal member for efficacious receipt of surgical instrumentation therethrough.

BRIEF DESCRIPTION OF THE DRAWINGS

Various embodiments are described herein with reference to the drawings wherein:

FIG. 5A is an exploded view with parts separated of a portion of a cannula assembly which is adapted to be associated with the seal assembly of FIG. 5;

FIG. 22a is an exploded view with parts separated of the dilator member with associated spring members of the seal assembly illustrated in FIG. 20;

FIG. 22b is an exploded view with parts separated of the dilator member with alternate embodiment spring members for use with the seal assembly illustrated in FIG. 20;

FIG. 32b is a cross-sectional view of the seal assembly of FIG. 30, which shows the instrument sealingly engaged by the seal member after dilation of the seal member has occured and the dilator has returned to its initial position;

FIG. 35 is an exploded view with parts separated of the dilator and block member of the seal assembly illustrated in FIG. 33;

FIGS. 36a–36c are side plan views of the dilator and block member of FIG. 35, illustrating movement of the dilator within the block member as the block member is moved in the direction of arrow "C";

DETAILED DESCRIPTION OF THE PREFERRED EMBODIMENTS

The seal assemblies described herein contemplate the use of all types of endoscopic and laparoscopic surgical instruments therethrough including, but not limited to, clip appliers, surgical staplers, lasers, endoscopes, laparoscopes, forceps, photographic devices, graspers, dissectors, suturing devices, scissors, and the like. All of such devices are referred to herein as "instruments".

The present seal assemblies, either alone or in combination with a seal system internal to a cannula assembly, provides a substantial seal between a body cavity of a patient and the outside atmosphere before, during and after insertion of an instrument through the cannula assembly. Moreover, the seal assemblies described herein are capable of accommodating instruments of varying diameters, e.g., from 5 mm to 15 mm, by providing a gas tight seal with each instrument when inserted. The flexibility of the present seal assembly greatly facilitates endoscopic surgery where a variety of instruments having differing diameters are often needed during a single surgical procedure.

Figure 1:
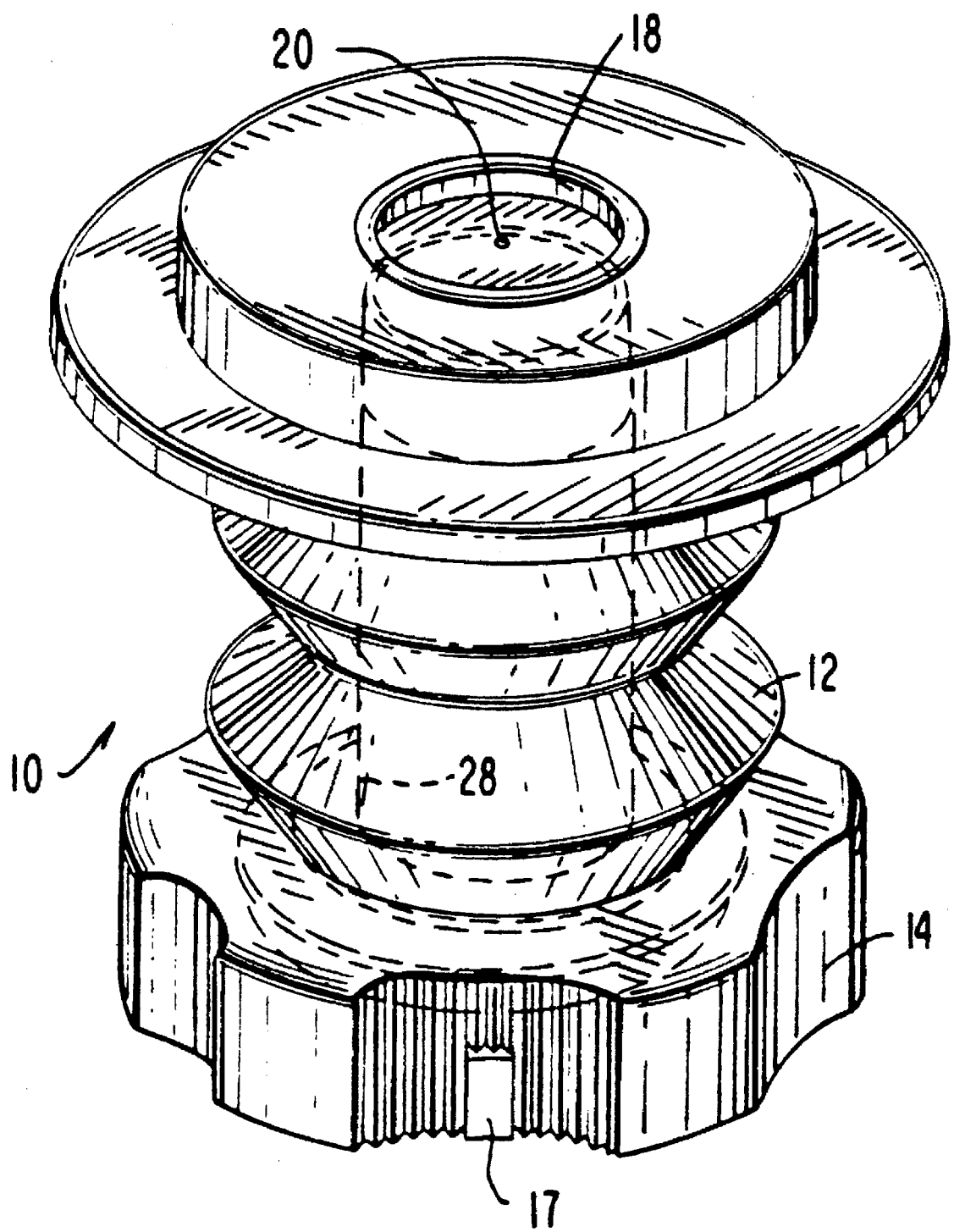
FIG. 1 is a perspective view of one embodiment of a seal assembly.

Referring to the drawings, in which like reference numerals identify identical or similar elements, FIGS. 1–4 illustrate a preferred seal assembly embodiment. Referring initially to FIG. 1 in conjunction with FIGS. 2 and 2A, seal assembly 10 includes a housing in the form of bellows 12 having knurled collar 14 attached thereto by any suitable method such as adhesives, heat welding, etc. Bellows 12 is fabricated from a resilient material, e.g., isoprene, to facilitate the movements described hereinbelow and is preferably about 1 to about 4 cm in axial dimension when at rest.

Knurled collar 14 serves to adapt bellows 12 for removable attachment to cannula assembly 16. In a preferred embodiment, seal assembly 10 is detachably mounted to cannula assembly 16 through a bayonet attachment, and knurled collar 14 facilitates the rotation of seal assembly 10 relative to cannula assembly 16 in effectuating the bayonet attachment. Printed indicia 17 and 17A assist the surgeon in aligning knurled collar 14 with cannula assembly 16 and inclined cam surface 45 guides an internal projection (not pictured) on knurled collar 14 to flat 47, whereby seal assembly 10 is detachably mounted to cannula assembly 16. Preferably, cannula assembly 16 includes a second inclined cam surface and flat on the opposite side thereof to cooperate with a second internal projection on hurled collar 14 to provide optimum stability to the interface between cannula assembly 16 and seal assembly 10. However, any suitable attaching method may be utilized, such as, for example, any quick connect mechanism.

Seal assembly 10 further includes a first seal member in the form of gasket 18, which is preferably fabricated from a resilient elastomeric material, e.g., polyisoprene. Gasket 18 is provided with aperture 20 formed centrally therethrough and preferably includes a proximally directed convolution which increases the flexibility and resilience thereof. Aperture 20 is preferably on the order of 4.5 mm in diameter so that aperture 20 has a diameter which is less than the smallest diameter instrument which is likely to be utilized therethrough during the course of an endoscopic surgical procedure. Gasket 18 is securely affixed to bellows 12 so as to form a fluid tight seal along periphery 22. Alternatively, gasket 18 may be formed integrally with bellows 12 by known manufacturing processes, e.g., injection molding.

Seal assembly 10 may also include additional sealing structures, such as gasket member 24, which may serve a variety of purposes. For example, gasket member 24 may simply function as a washer to ensure that seal assembly 10 is internally sealed. Alternatively, gasket member 24 may serve to sealingly engage instruments inserted through seal assembly 10 when aperture 20 of gasket 18 is stretched around the exterior face of dilator 28, as discussed below. Gasket member 24 is also preferably fabricated from a resilient elastomeric material, e.g., polyisoprene. An aperture 26 is formed through the center of gasket member 24 having a greater diameter than the diameter of aperture 20 in gasket 18. For example, if gasket member 24 is intended to sealing engage instruments passed therethrough and if aperture 20 is on the order of 4.5 mm, aperture 26 is preferably on the order of 9 to 10 mm. In this way, gasket 24 will sealingly engage surgical instruments which are inserted through seal assembly 10 having a diameter of 9 mm and greater.

Seal assembly 10 further includes dilating member in the form of dilator 28 which is preferably made of a rigid polymeric material, e.g., ABS (acrylonitrile-butadiene-styrene) or a suitable polycarbonate material. Dilator 28 has a passageway 30 formed therein which allows for passage of instruments therethrough. Flange 32 is formed at distal end 34 of dilator 28 and is configured and dimensioned for attachment to knurled collar 14, e.g., by an appropriate adhesive, sonic welding or the like. Inner wall 33 of dilator 28 is preferably of substantially uniform diameter, whereas the outer face 35 of dilator 28 preferably includes an inwardly tapered portion 39 at its proximal end. Inwardly tapered portion 39 facilitates interaction of dilator 28 with gasket 18 when dilator 28 acts to spread aperture 20 thereof. The inner diameter of dilator 28 is selected to accommodate free passage of the instrumentation to be used therethrough and is typically on the order of 13 to 14 mm. Different internal diameters may be selected, however, based on the instrumentation seal assembly 10 is intended to accommodate. Dilator 28 also optionally includes vent 29 which permits gas communication therethrough. Vent 29 facilitates the collapse of bellows 12, as discussed below, by providing a path of egress for the air located between outer face 35 of dilator 28 and bellows 12. Optionally, a plurality of vents may be circumferentially and/or axially spaced around dilator 28 to facilitate such air egress.

Figures 2, 2A:
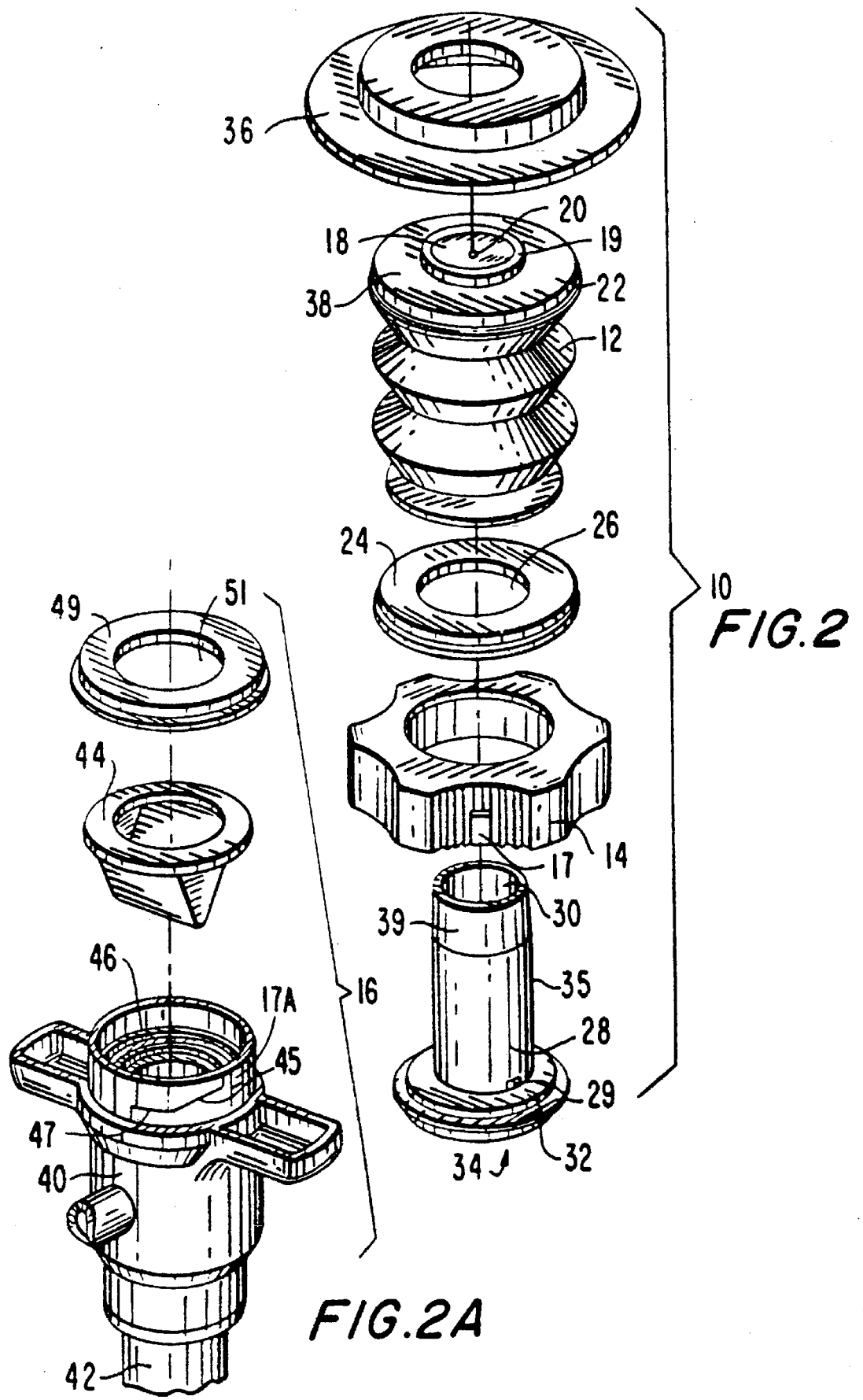
FIG. 2 is an exploded view with parts separated of the embodiment of FIG. 1.
FIG. 2A is an exploded view with parts separated of a portion of a cannula assembly which is adapted to be associated with the seal assembly of FIG. 2.

Referring to FIG. 2A, cannula assembly 16 includes cannula housing 40 and cannula 42 which is attached thereto and which extends distally therefrom. Cannula assembly 16 preferably includes a second seal member, in the form of distally directed duckbill 44 mounted in interior region 46 of cannula housing 40. Duckbill 44 provides a substantially fluid-tight seal when communicating with an insufflated body cavity to substantially prevent escape of gases and fluids from inside the body cavity when no instrument is present in cannula assembly 16. Cannula assembly 16 also preferably includes a second gasket 49 fabricated from a resilient elastomeric material, e.g., polyisoprene. Second gasket 49 is provided with aperture 51 formed centrally therethrough. The diameter of aperture 51 may range widely, e.g. from 3 mm to 15 mm, based on the diameter of cannula 42 which defines the instrument sizes cannula assembly 16 is generally intended to accommodate. Depending on the diameter of aperture 51, second gasket 49 is adapted to sealingly engage surgical instruments of greater diameter with respect thereto.

Figure 3:
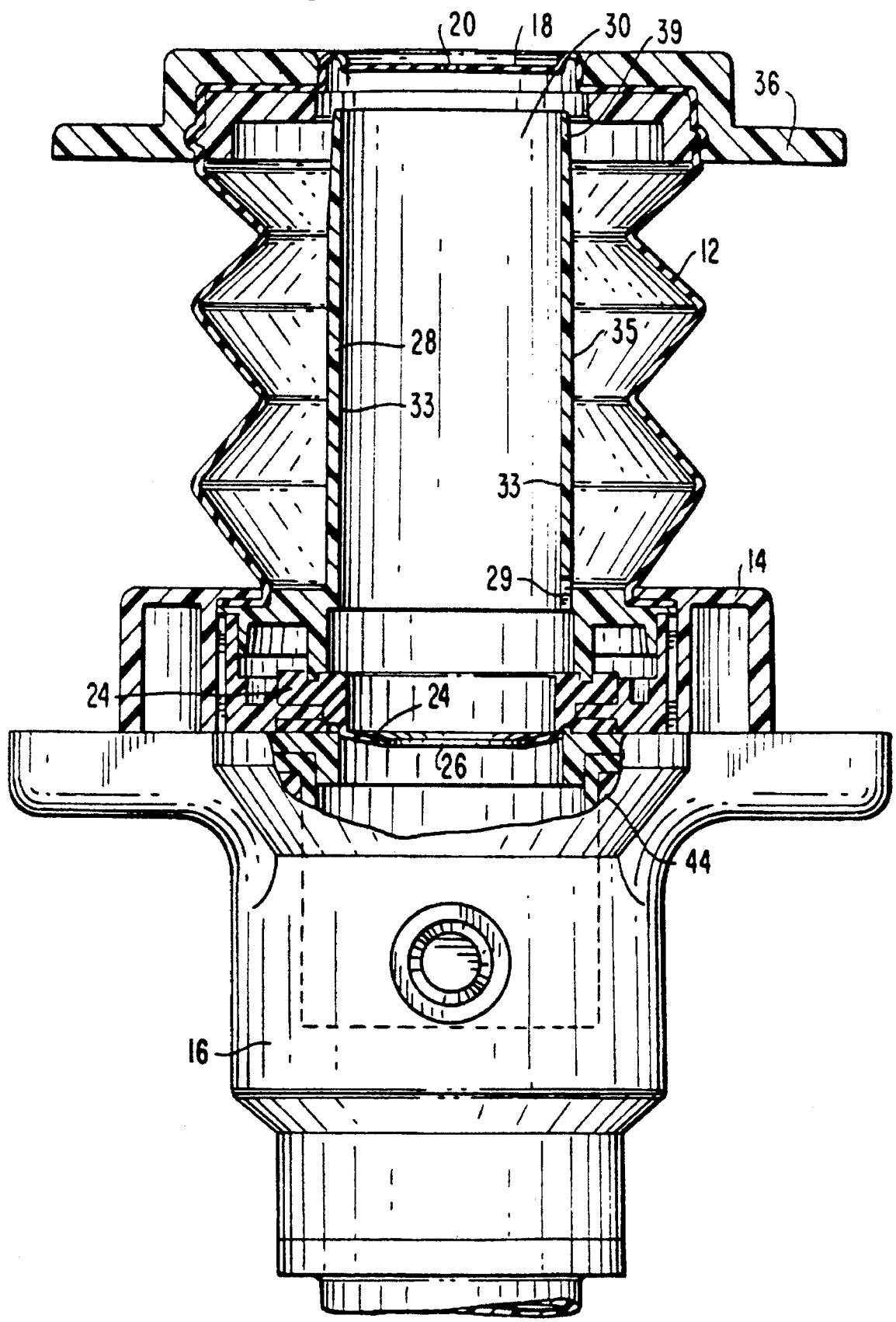
FIG. 3 is a partial cross-sectional view of the seal assembly illustrated in FIGS. 1 and 2 associated with the cannula assembly of FIG. 2A, which shows a seal member in a non-dilated position.
Figure 4:
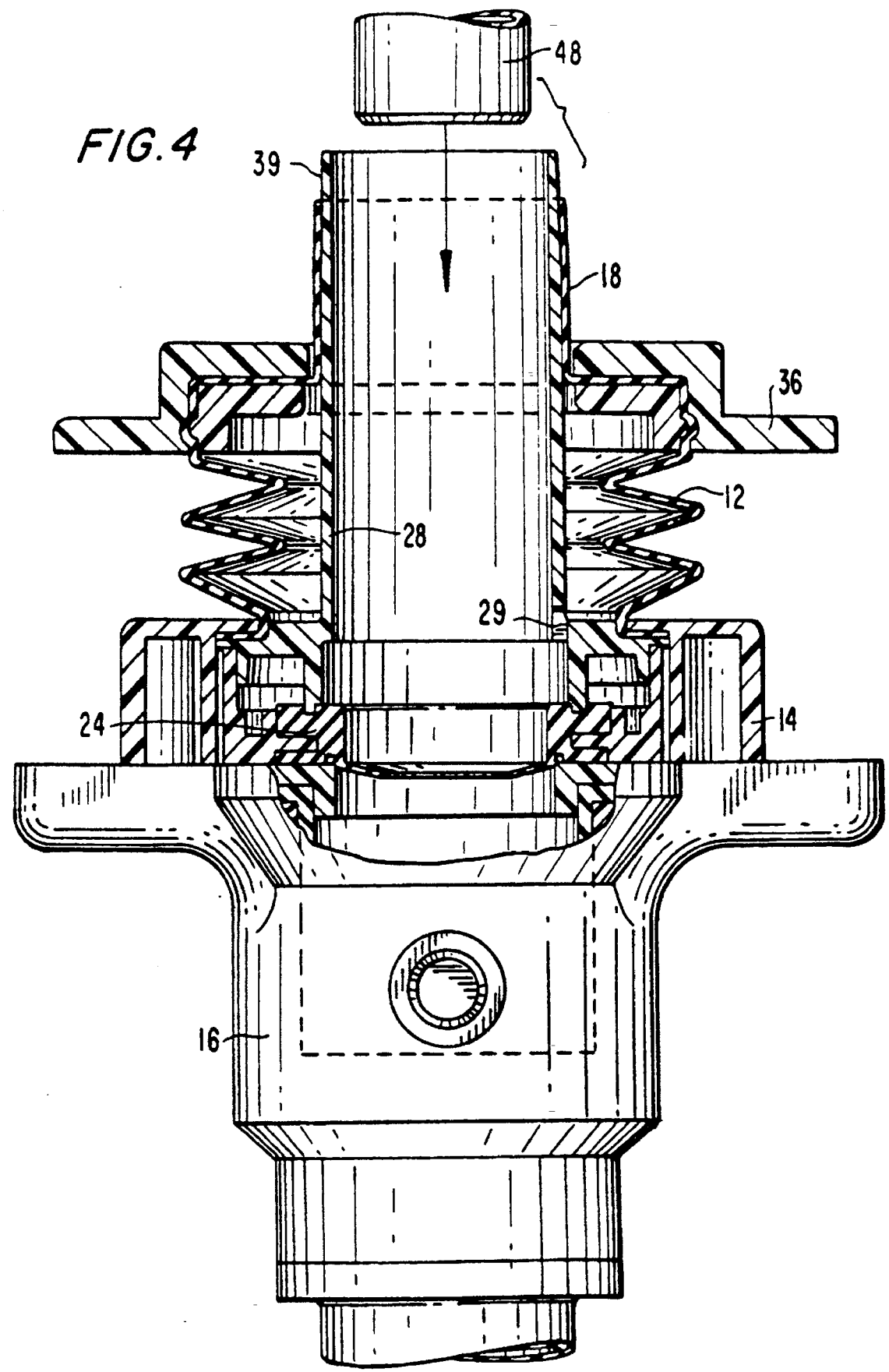
FIG. 4 is a partial cross-sectional view of the seal assembly similar to FIG. 3, except that the flange of the seal assembly is shown depressed so that the aperture of the seal member is dilated to the size of the opening of the dilator member.

The operation of seal assembly 10 in conjunction with cannula assembly 16 will now be described with reference to FIGS. 3 and 4. Prior to insertion of a surgical instrument, such as instrument 48, duckbill member 44 provides a fluid-tight seal to cannula assembly 16. Seal assembly 10 is mounted to cannula assembly 16 and is in a first or at-rest position with bellows 12 fully extended in the axial direction as shown in FIG. 3. In this position, seal assembly 10 can receive surgical instrumentation having a diameter which closely corresponds to the diameter of aperture 20 in gasket 18 with minimal insertion force required. Thus, if the diameter of aperture 20 is on the order of 4.5 mm, seal assembly 10 may receive surgical instruments of up to about 7 mm with minimal insertion force. However, with larger diameter instruments, e.g., instruments on the order of 10 to 12 mm in diameter, the insertion force required by the user with seal assembly 10 in the position shown in FIG. 3 increases substantially.

To reduce the force required to introduce such a larger diameter instrument 48 through aperture 20, flange 36, which is fabricated from a rigid polymeric material, e.g., ABS, is urged distally by the user, thereby translating gasket 18 with respect to dilator 28. This relative translation causes aperture 20 of gasket 18 to stretch around the inwardly tapered portion 39 of dilator 28, as shown in FIG. 4. This relative translation also causes bellows 12 to collapse and causes air egress through vent 29 into passage 30 of dilator 28, thereby preventing undesirable air compression in the region between dilator 28 and bellows 12 which would increase the force required to translate flange 36. As shown in FIG. 4, the resilience of gasket 18 allows distortion of a portion of gasket 18 to a substantially tubular orientation in conforming abutment with the outer face 35 of dilator 28. Instrument 48 can now be inserted through passage 30 within dilator 28 of seal assembly 10 and through cannula assembly 16 with minimal insertion force. Gasket member 24 and/or second gasket 49 sealingly engage instrument 48 as it passes therethrough. Thus, at the point instrument 48 passes through duckbill member 44, a fluid-tight seal within cannula assembly 16 and seal assembly 16 is nonetheless ensured by the interaction between instrument 48 and gasket member 24 and/or second gasket 49.

Once instrument 48 is inserted through dilator 28, flange 36 may be released by the user. Depending on the degree to which bellows 12 was collapsed and the degree of resilience of gasket 20 and bellows 12, bellows 12 may resume its initial at-rest position (as shown in FIG. 3) without further impetus by the user. However, if the forces exerted by gasket 20 and bellows 12 are insufficient to automatically return bellows 12 to its initial at-rest position, the user may raise flange 36 relative to cannula assembly 16, thereby inducing bellows 12 to resume its at-rest position. In either event, return of bellows 12 to its initial at-rest position allows gasket 18 to close around instrument 48, providing an ancillary fluid tight seal. The resilience of gasket 18 and the presence of convolution 19 advantageously facilitate some degree of axial movement of instrument 48 with respect to seal assembly 10 without any translation of instrument 48 with respect to gasket 18. Rather, gasket 18 retains a fixed arcuate line of contact with instrument 48 by resiliently deflecting with the movement of instrument 48, alternately assuming convex and concave orientations with the axial movement of instrument 48. Thus, the resilience of gasket 18 together with the presence of convolution 19 reduces the force required for limited movements of instrument 48, while also serving to stabilize instrument 48 within seal assembly 10 and cannula assembly 16.

A printed indicia, e.g., a transverse line, may be provided on outer face 35 of dilator 28 to indicate the point at which bellows 12 is sufficiently collapsed to prevent its automatic return to its initial at-rest position. Thus, if the user desires to utilize instrument 48 within the body cavity with seal assembly 10 in the position shown in FIG. 4, i.e., with bellows 12 in its collapsed position, the user may simply urge flange 36 distally to the extent necessary to move gasket 18 below the printed indicia on the outer face 35 of dilator 28.

If bellows 12 is returned to its initial at-rest position and it is desired to remove instrument 48 from cannula assembly 16 and seal assembly 10, the user may repeat the steps described hereinabove to expand the diameter of aperture 20, thereby facilitating passage of instrument 48 with minimal force. Similarly, if it is desired to remove a specimen from within the body cavity, the user may repeat the steps described hereinabove to expand the diameter of aperture 20 to facilitate specimen passage. The user may also, if desired and in the absence of a surgical instrument inserted therethrough, detach seal assembly 10 from cannula assembly 16 at any point during the surgical procedure to advantageously employ surgical instruments through low profile cannula assembly 16.

Figure 5:
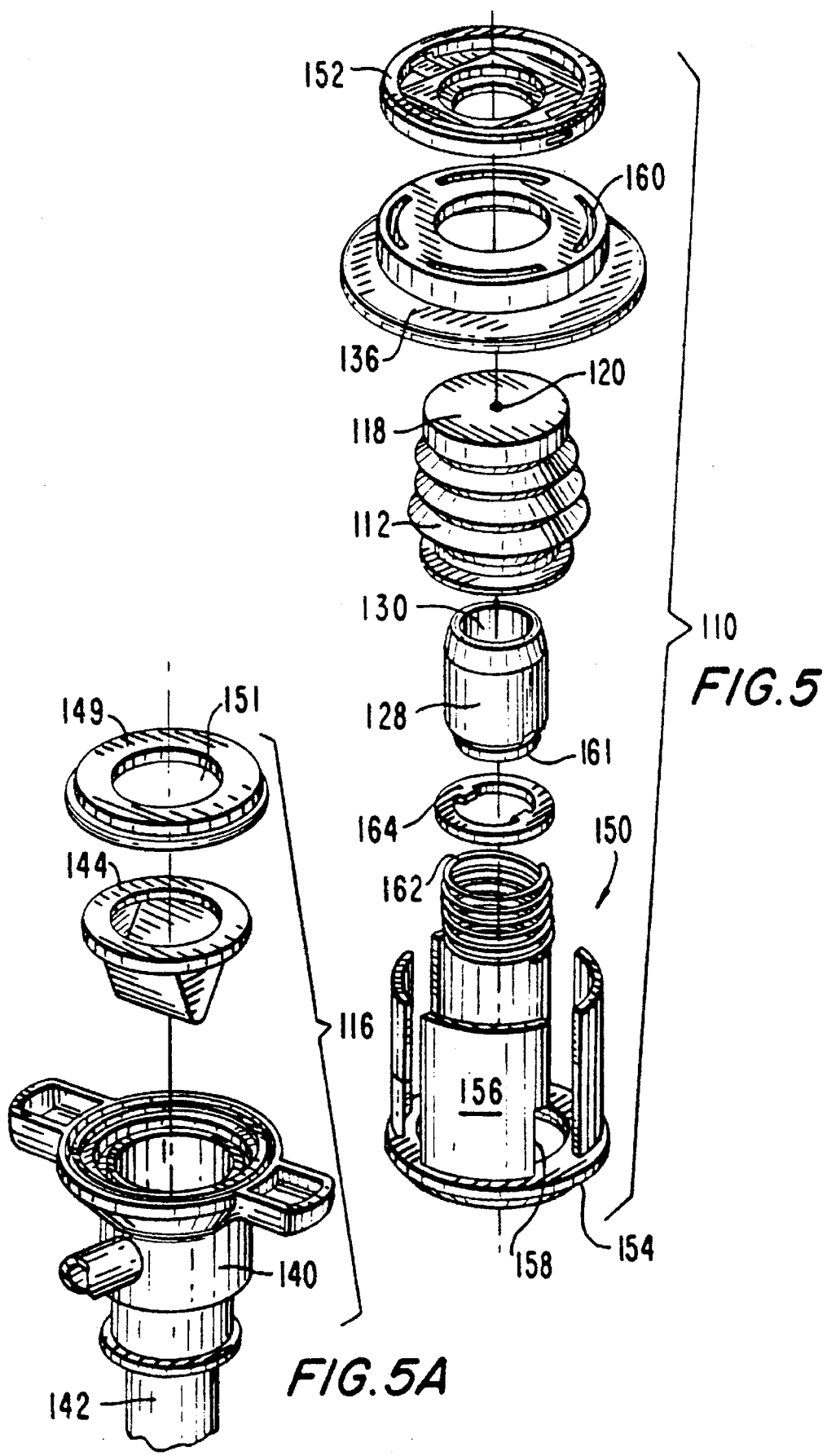
FIG. 5 is an exploded view with parts separated of another seal assembly embodiment.
Figure 6:
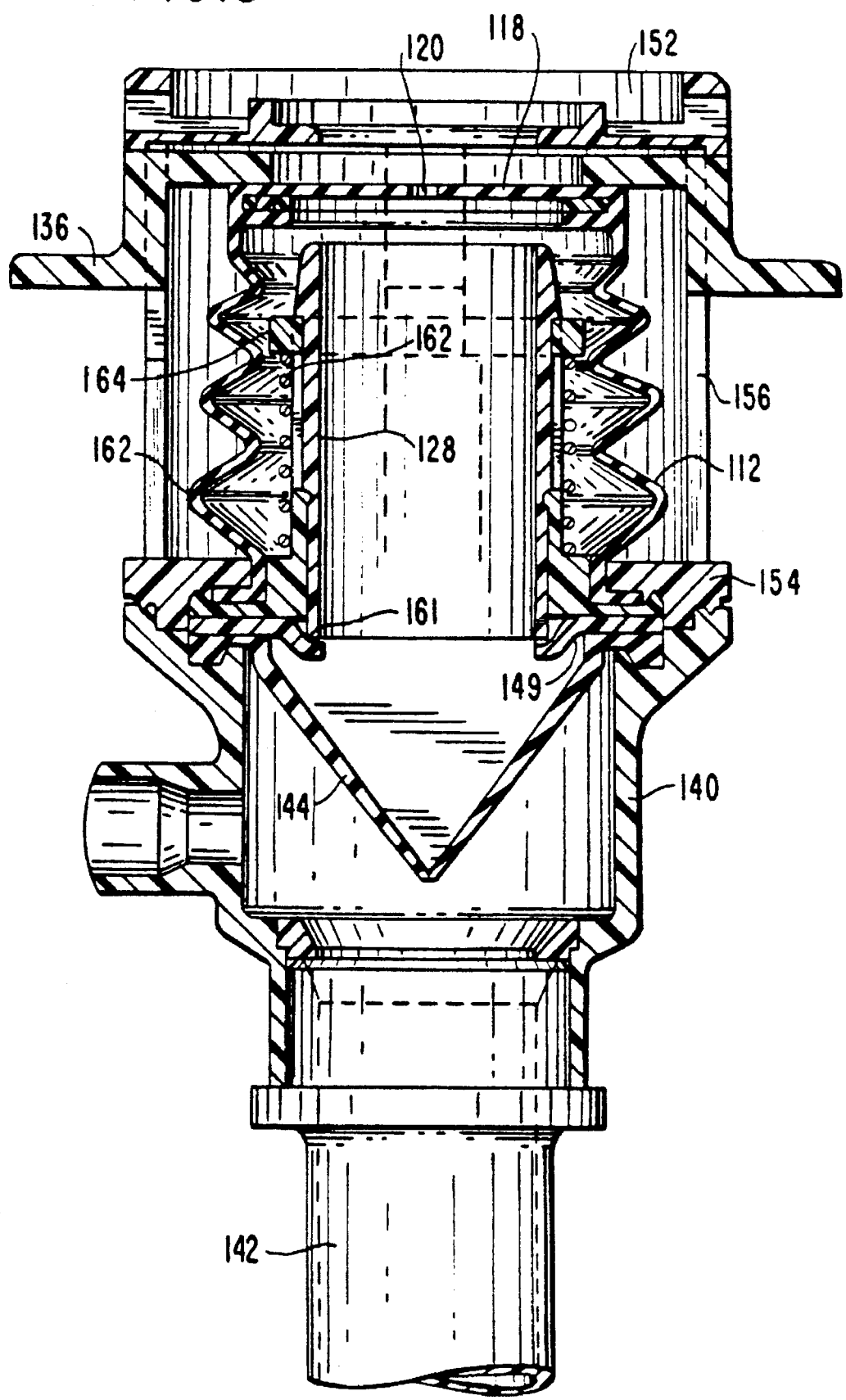
FIG. 6 is a partial cross-sectional view of the embodiment of FIG. 5, which shows a seal member of the embodiment in a non-dilated position.
Figure 7:
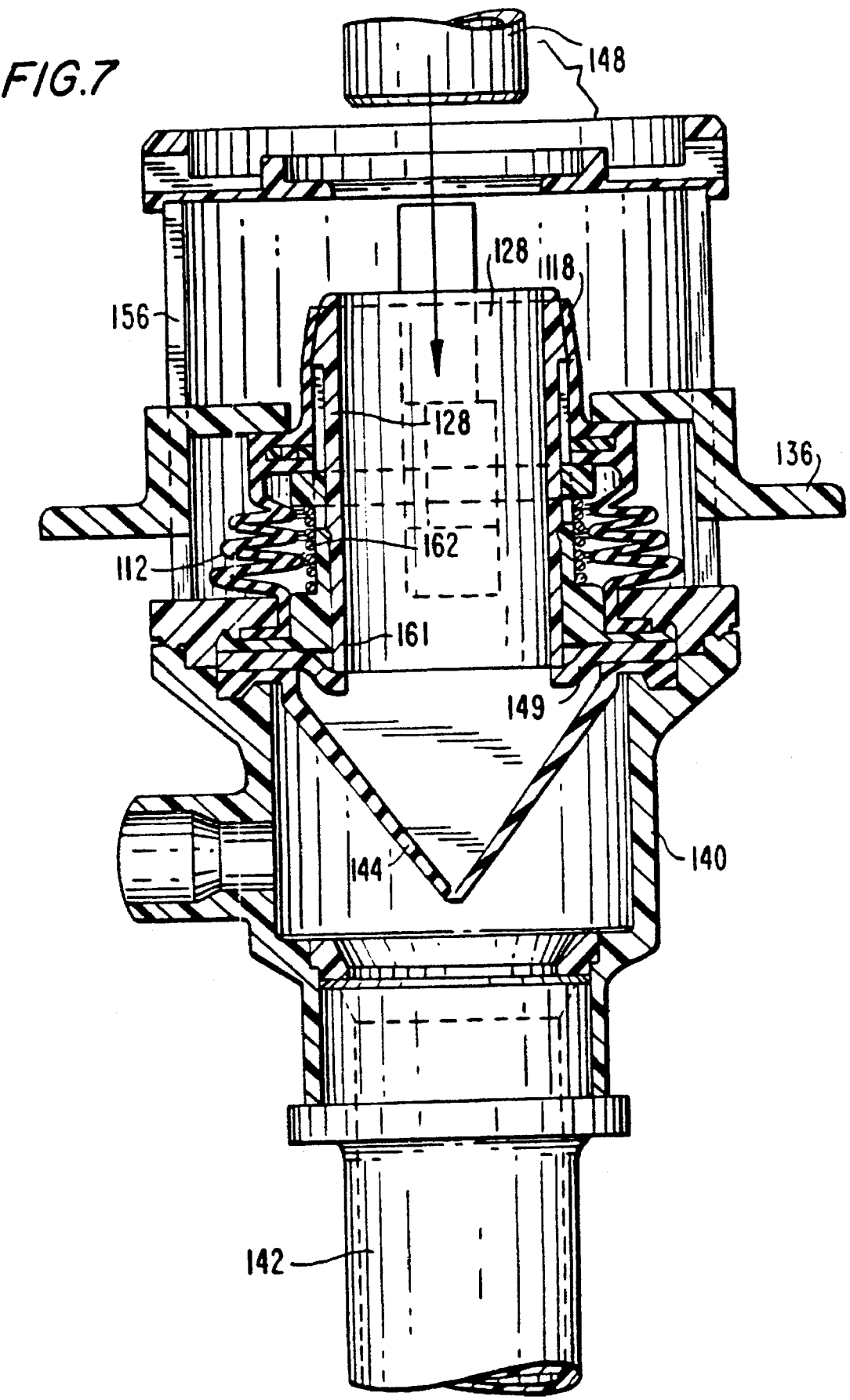
FIG. 7 is a partial cross-sectional view of the embodiment of FIG. 5, which shows the flange of the seal assembly depressed so that the aperture of the seal member is dilated to the size of the opening of the dilator member.

Another seal assembly embodiment is illustrated in FIGS. 5–7. Seal assembly 110 is similar to seal assembly 10. Structures which are similar to structures in seal assembly 110 are designated with reference numerals similar to those of seal assembly 10 except a leading "1" has been added. With the exceptions noted below, operation of seal assembly 110, as shown in FIGS. 6 and 7, is as described in connection with seal assembly 10 and FIGS. 3 and 4 hereinabove.

Referring to FIGS. 5 and 5A, seal assembly 110 includes a rigid outer structure which includes frame 150 which is preferably made of ABS or a polycarbonate material. Frame 150 is in the form of a cage which is bounded at its proximal end by face 152 which is preferably bonded thereto, e.g., by an adhesive, sonic welding or the like. Frame 150 includes an annular base portion 154 to which dilator 128 is affixed, e.g., by an adhesive or sonic welding, and four rigid, proximally-directed arcuate portions 156, each having a notch 158 formed thereon. Flange 136 is provided with four arcuate slotted cut-outs 160 which may be cooperatively aligned with arcuate portions 156.

Dilator 128 includes a substantially tubular, distally-directed extension 161 which extends distally beyond the annular base portion 154 of frame 150. Extension 161 serves to dilate aperture 151 of gasket member 149 when seal assembly 110 is mounted to cannula assembly 116. The dilation of aperture 151 by extension 161 further reduces the force required to introduce an instrument therethrough. The presence of extension 161 on dilator 128 militates in favor of returning bellows 112 to its initial at-rest position after an instrument is inserted therethrough so that gasket 118 may sealingly engage the shaft thereof. In that regard, bellows 112 is biased proximally toward its initial at-rest position by spring 162 and bearing ring 164.

When urged distally to collapse bellows 112 and expand aperture 120 of gasket 118 around dilator 128, flange 136 may be rotated clockwise, thereby locking flange 136 under notches 158 against the bias of spring 162, bearing ring 164, and the resilience of bellows 112 and gasket 118. The interaction between flange 136 and notches 158 of frame 150 provides an alternative method for maintaining bellows 112 in its collapsed position. As noted above, the retention of any of the bellows embodiments described herein in a collapsed configuration may be advantageous if it is desired to utilize a surgical instrument within the body cavity without the shaft of the instrument being engaged by the gasket (18, 118). With flange 136 locked under notches 158, aperture 120 is maintained in its expanded position around the exterior face 135 of dilator 128 until released by the user.

Figure 8:
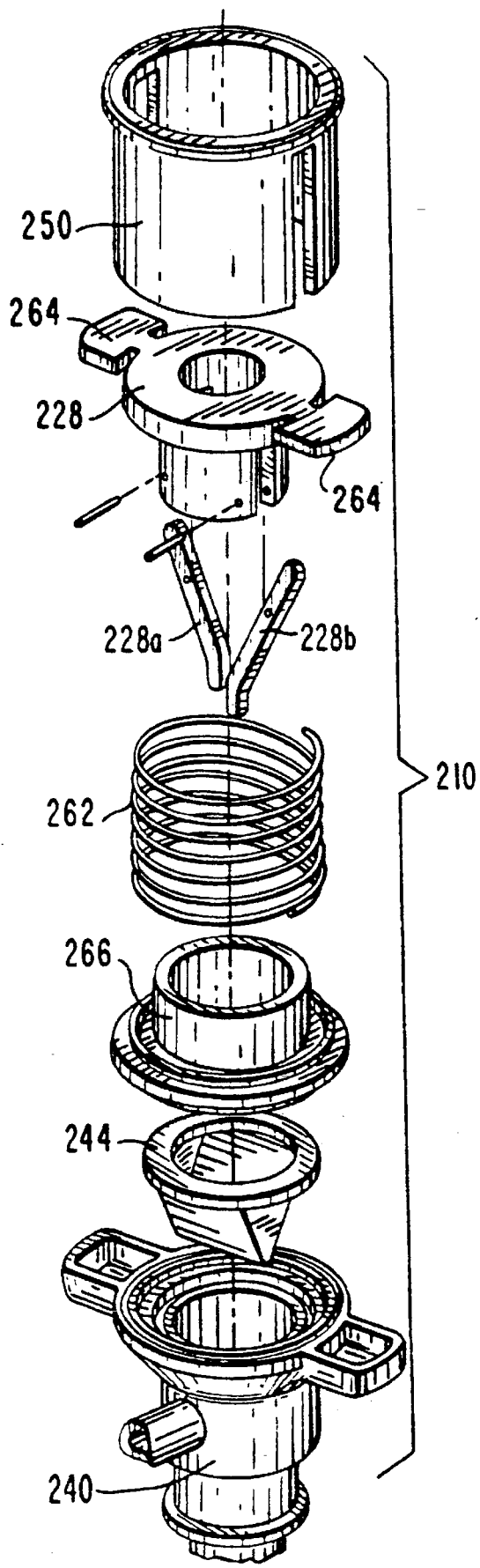
FIG. 8 is an exploded view with parts separated of another seal assembly embodiment.
Figure 9:
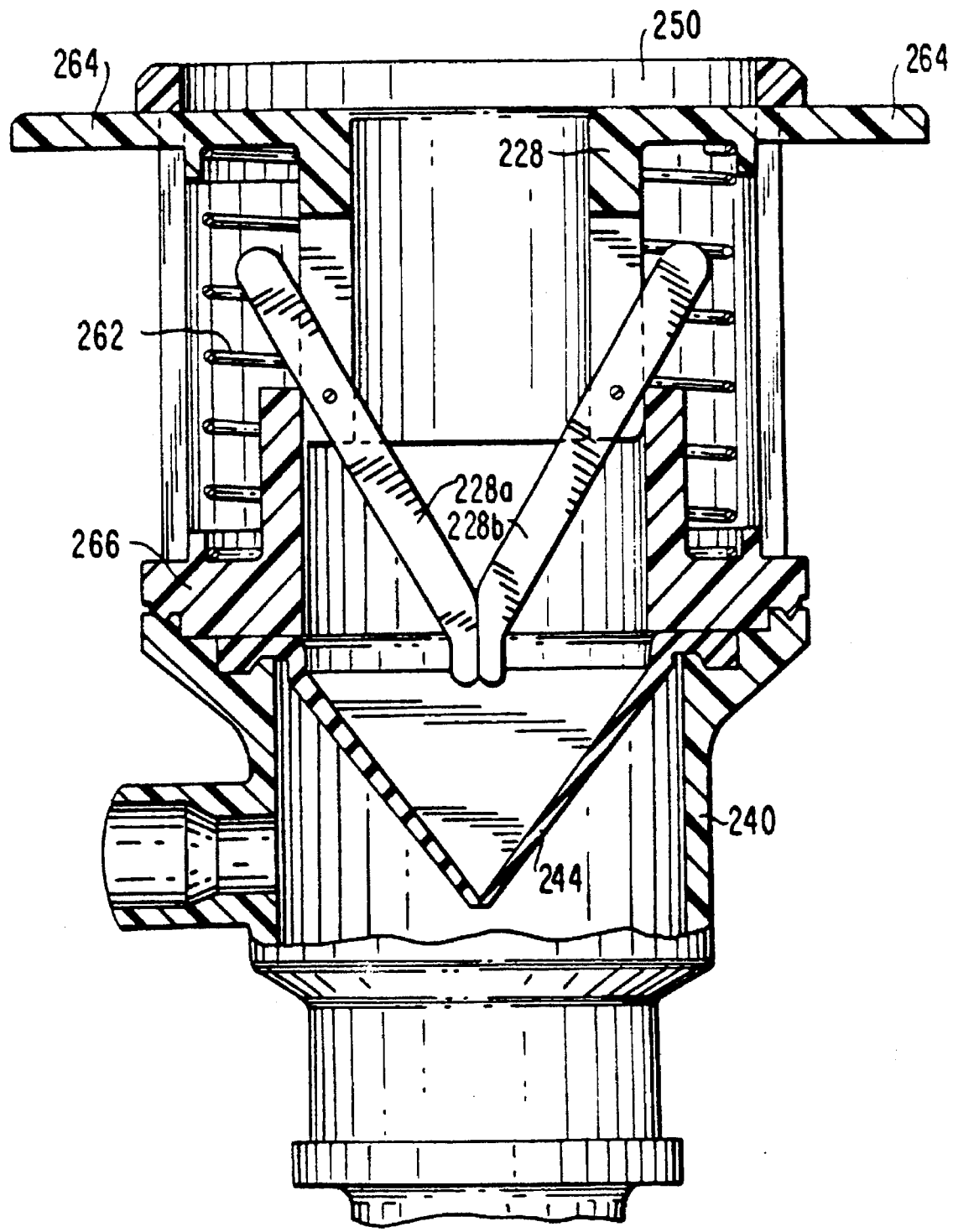
FIG. 9 is a partial cross-sectional view of the embodiment of FIG. 8, which shows a seal member of the embodiment in a non-dilated position.
Figure 10:
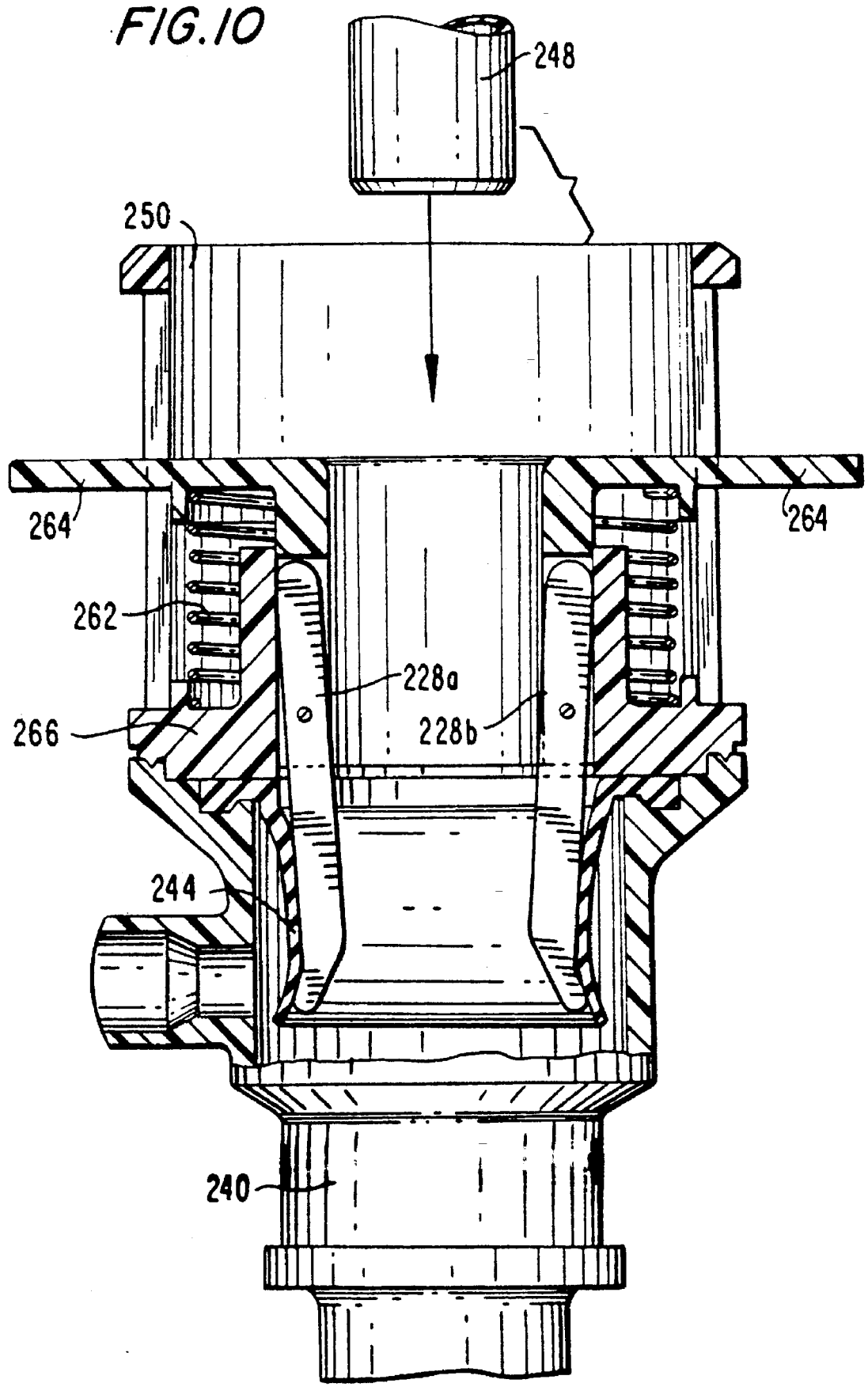
FIG. 10 is a partial cross-sectional view of the embodiment of FIG. 8, which shows the flange of the seal assembly depressed so that the aperture of the seal member is dilated by the pivoting dilator members.

Another seal assembly embodiment is illustrated in FIGS. 8–10 as seal assembly 210 which is similar in certain respects to seal assemblies 10 and 110. Structures which are similar to corresponding structure in seal assemblies 10 and 110 are designated by the same numerals except that a leading "2" has been added for clarity and consistency.

In seal assembly 210, dilator 228 is movable relative to duckbill 244 which performs the assembly's sealing function. Other seal members may be provided in addition to or in place of duckbill 244, as for example, one or more gaskets as described hereinabove. Dilator 228 is provided with extended members 228a and 228b pivotably mounted thereto and tab portions 264 to facilitate movement of dilator 228 in a distal direction. Dilator 228 is biased in a proximal direction by spring 262 which bears against collar 266. Collar 266 also serves as a camming surface for extended members 228a and 228b during distal motion of dilator 228 as best be seen in FIGS. 9 and 10.

In operation, as illustrated in FIGS. 9 and 10, when it is necessary or desirable to insert a large diameter instrument, e.g., an instrument having a diameter on the order of 7 to 15 mm, dilator 228 is moved distally by advancing tabs 264 relative to cannula assembly 240. Extended members 228a and 228b contact collar 266 and are cammed thereby so that extended members 228a and 228b pivot to spread open the slit of duckbill 244 as illustrated in FIG. 10. Instrument 248 is then inserted through seal assembly 210 and tab portions 264 are released to allow duckbill 244 to close around instrument 248. As noted above, other seal configurations may be readily used to supplement or replace duckbill 244. For example, a planar seal member having a central aperture or slit may be utilized in which event extended members 228a and 228b will serve to expand the size of the aperture or slit in the same manner as described for expanding the slit of duckbill 244.

Figure 11:
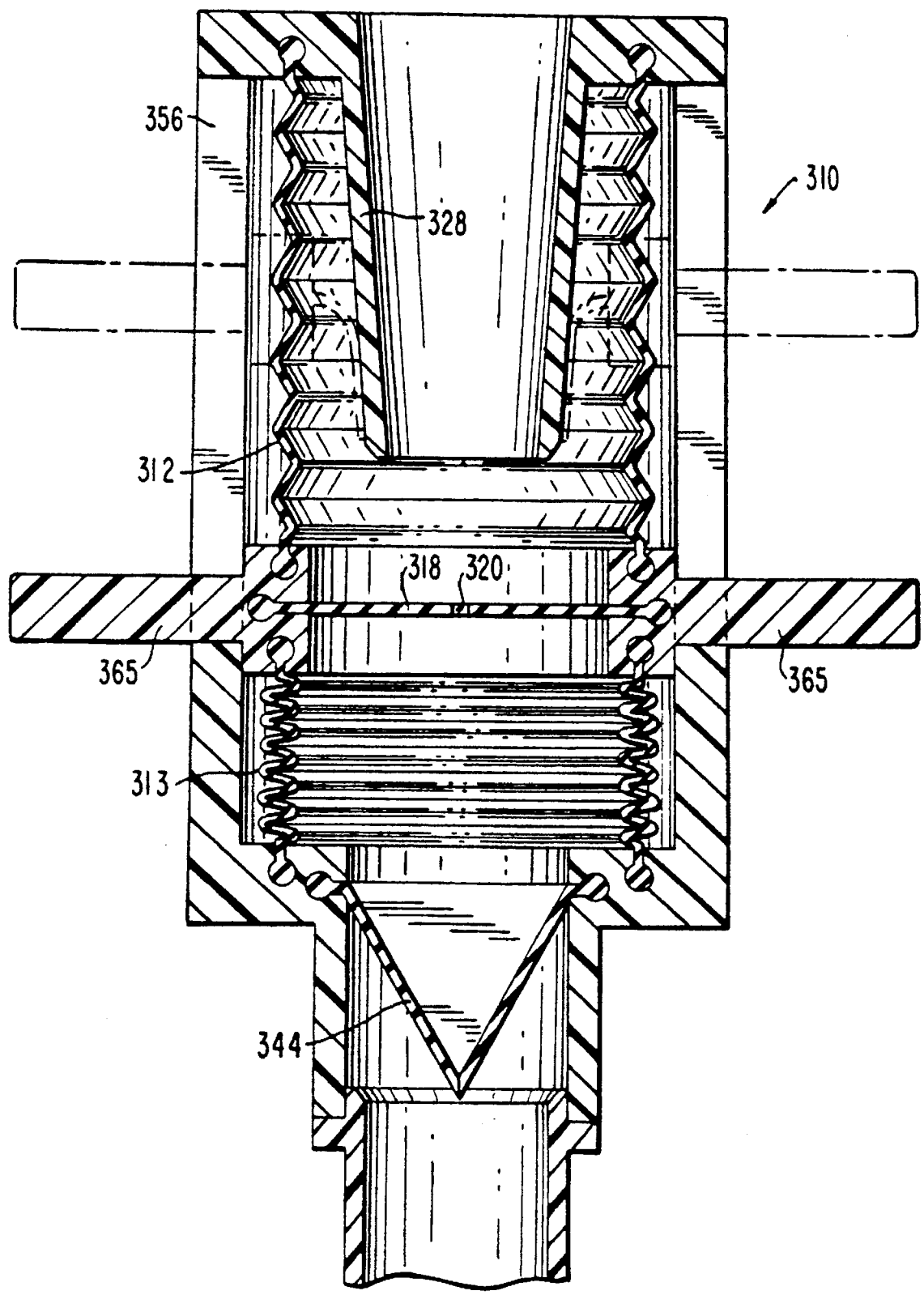
FIG. 11 is a cross-sectional view of another seal assembly embodiment.

Another seal assembly embodiment is illustrated in FIG. 11 as seal assembly 310 which is most closely related in structure and operation to seal assembly 110 of FIGS. 5–7, described above. Seal assembly 310 differs from seal assembly 110 in that dilator 328 is conical and is fixed with respect to the frame 356. Gasket 318 is positioned distally of dilator 328 when seal assembly 310 is in its initial at-rest position and is adapted for axial movement with respect thereto. Additional bellows 313 is secured to seal carrier flange 365 at its proximal end and to the distal portion of frame 356 so as to form a fluid-tight passageway therewithin. In order to dilate aperture 320 of seal 318, seal carrier flange 365 is pulled proximally as shown in phantom lines in FIG. 11, thereby translating gasket with respect to dilator 328 and expanding aperture 320 therearound. Proximal translation of seal carrier flange serves to collapse bellows 312 while simultaneously axially extending additional bellows 313.

Figure 12:
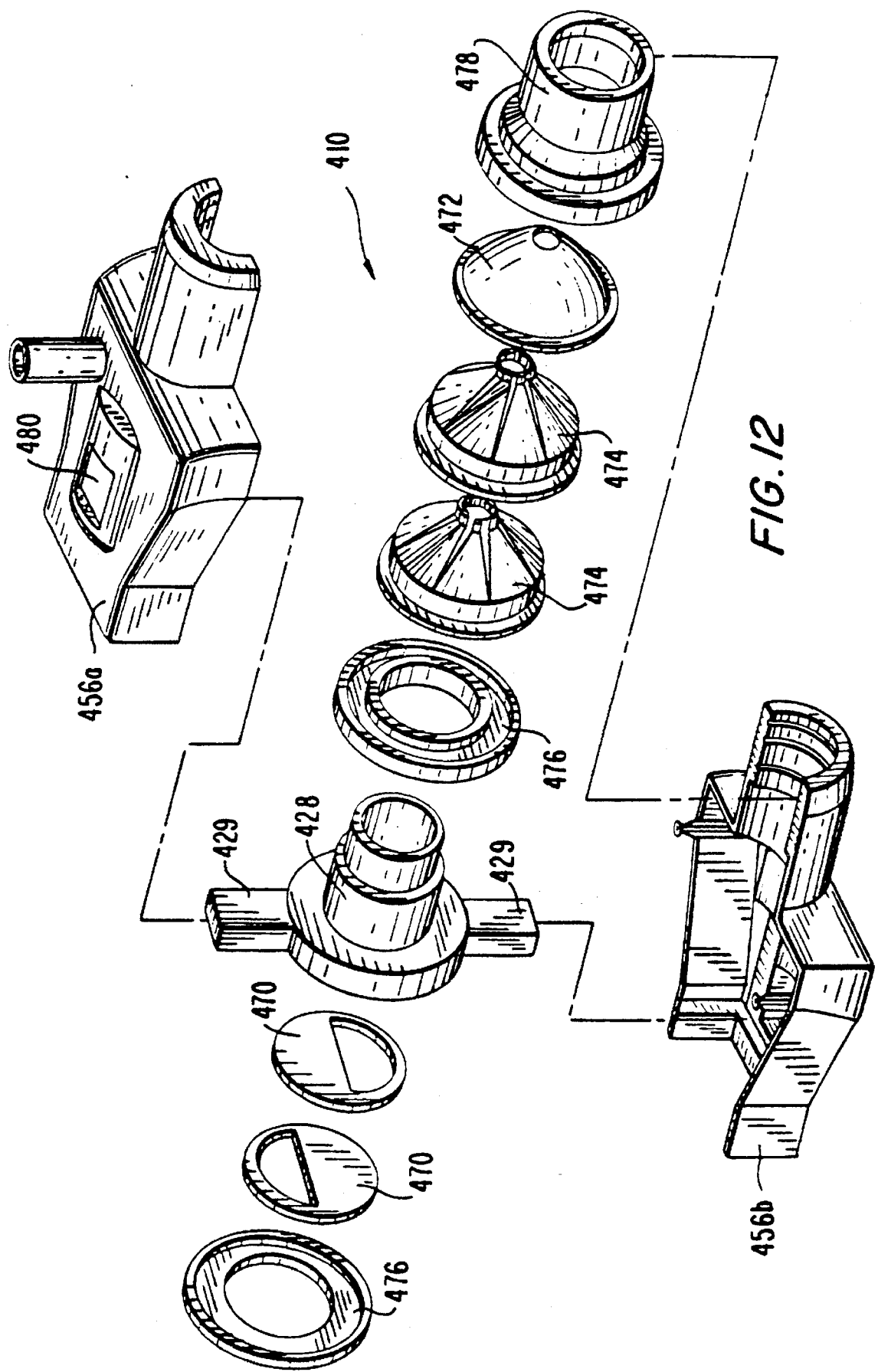
FIG. 12 is an exploded view with parts separated of another seal assembly embodiment.
Figure 13:
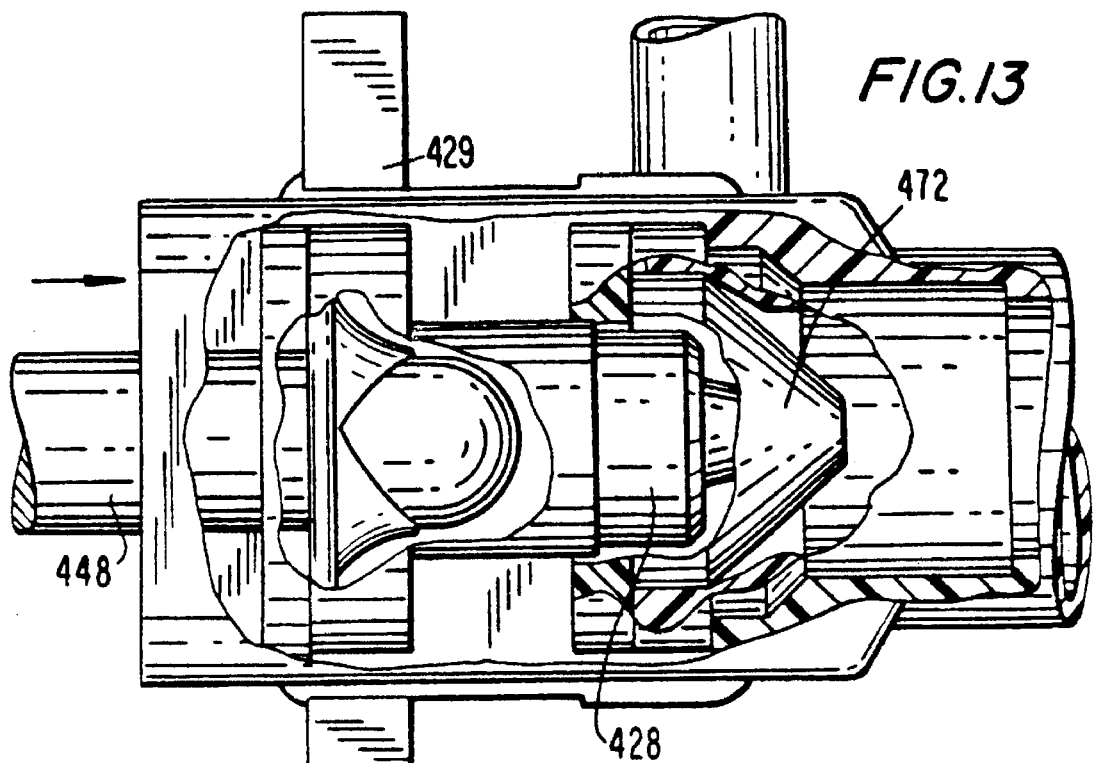
FIGS. 13 and 14 are progressive partial cross-sectional views of the embodiment of the seal assembly of FIG. 12, which show the operation of the seal assembly as a surgical instrument is inserted therein.
Figure 14:
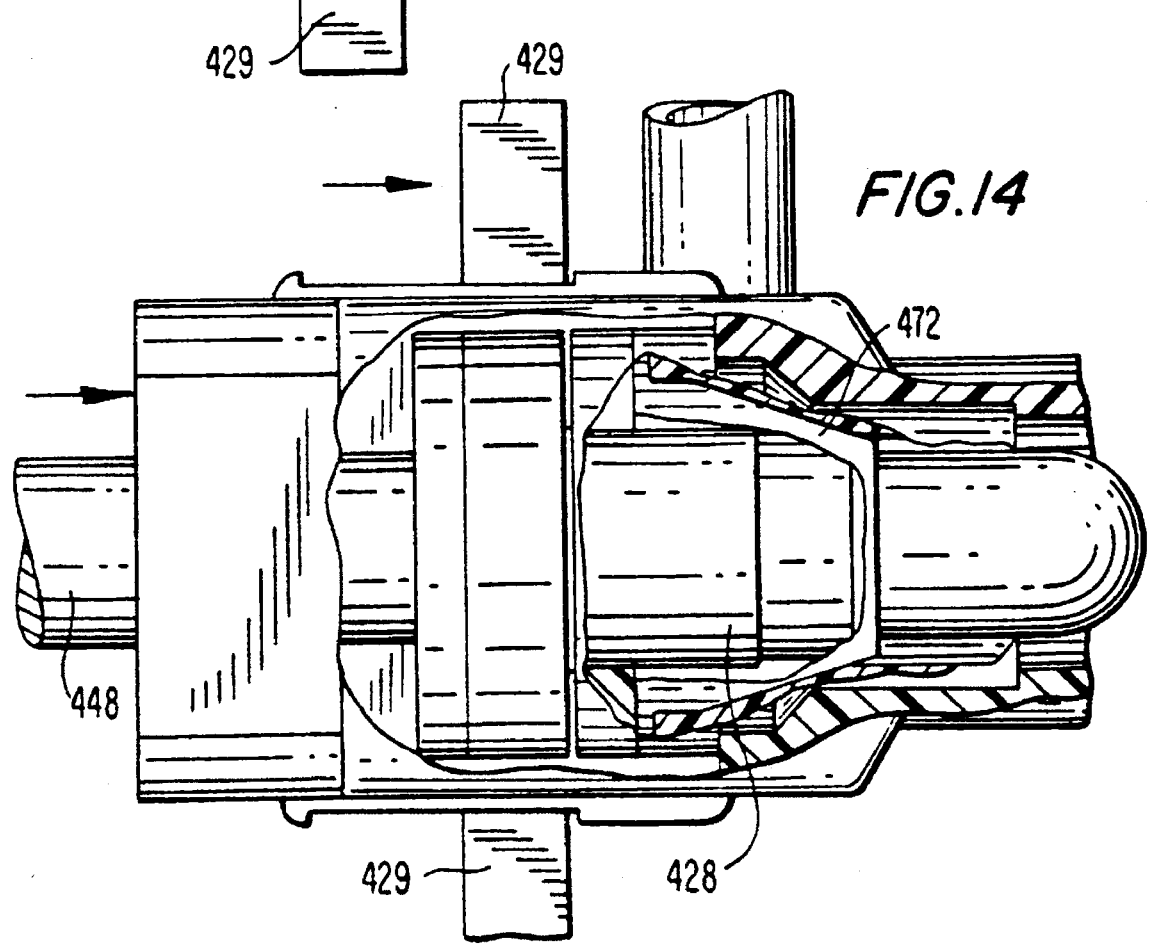
Figure 15:
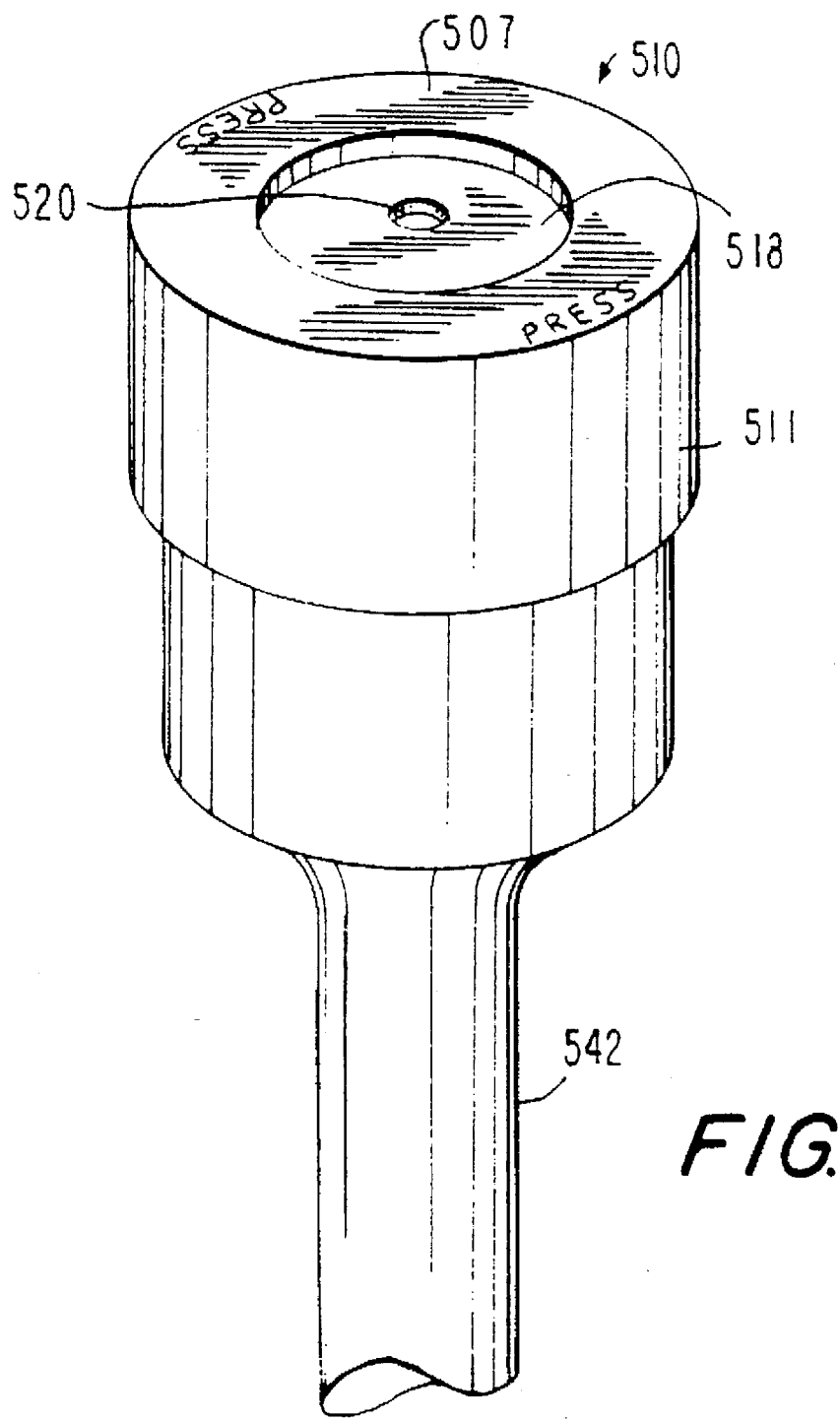
FIG. 15 is a perspective view of another seal assembly embodiment.
Figure 16:
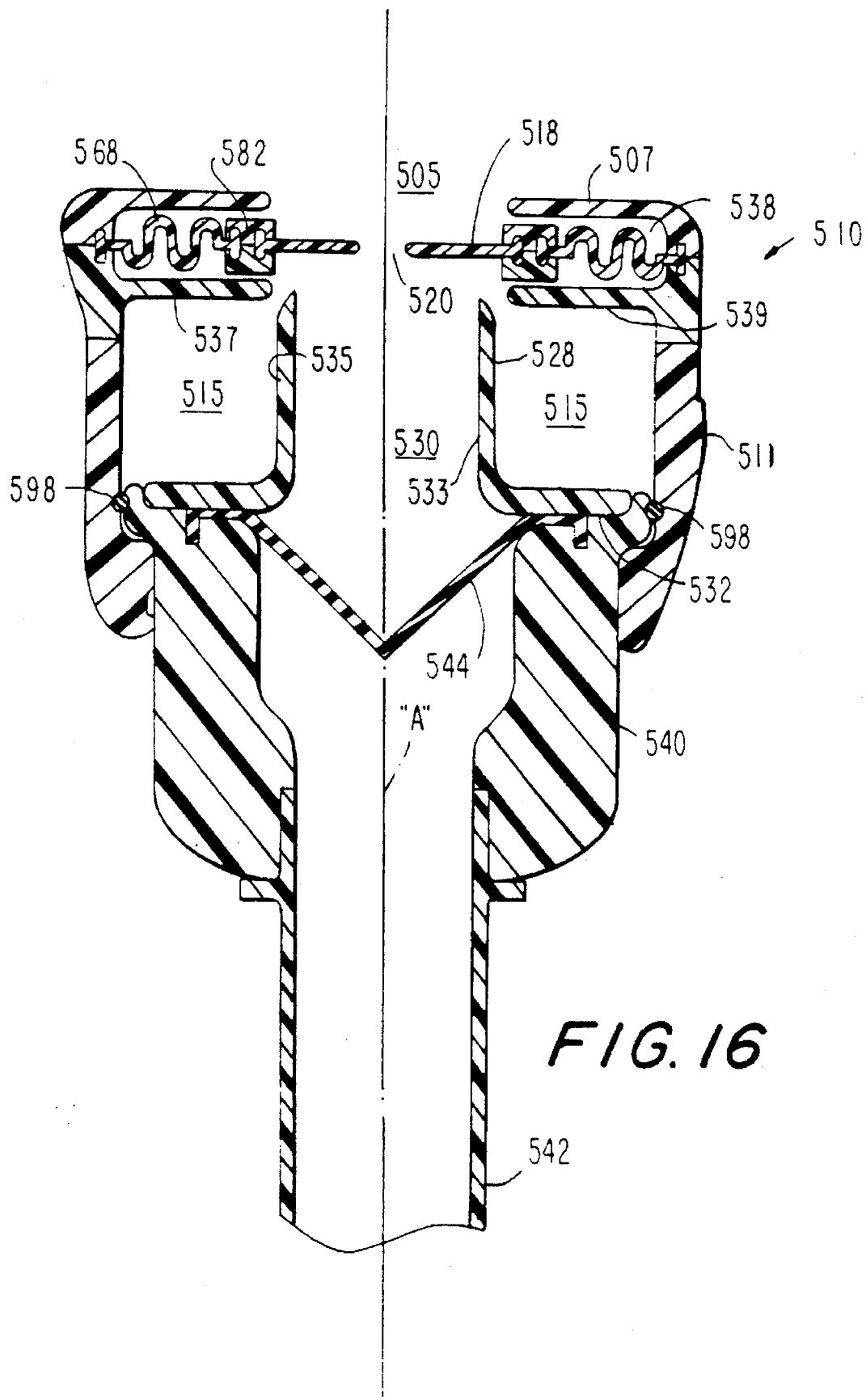
FIG. 16 is a cross-sectional view of the seal assembly illustrated in FIG. 15, which shows a seal member in a non-dilated position.
Figure 17:
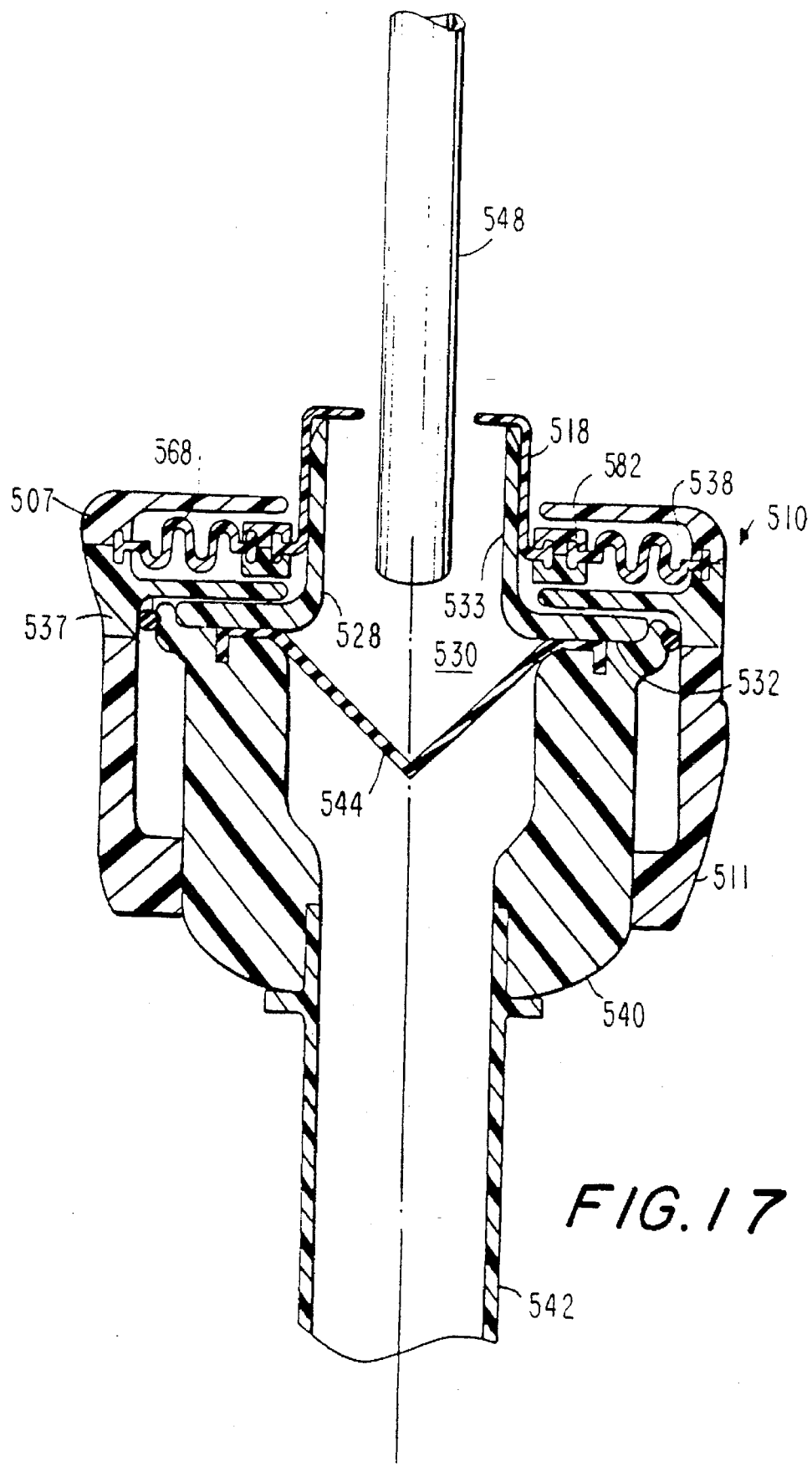
FIG. 17 is a cross-sectional view of the seal assembly of FIG. 15, which shows the end cap of the seal assembly depressed so that the seal member has moved into contact with the dilator member so that the aperture of the seal member is stretched by the dilator member.

Another seal assembly embodiment is illustrated in FIGS. 12 to 14 as seal assembly 410 which is incorporated in cannula housing sections 456a and 456b. A plurality of sealing elements such as overlapping sealing members 470 and conical gasket 472 are provided, as well as reinforcing and penetration prevention members such as conical members 474 which include overlapping tab portions for spreading and protecting gasket 472. Members 476, preferably of an elastomeric material, are provided to substantially seal the interior passageway formed by the tubular extension of cannula housing sections 456a and 456b. Collar member 478 is provided and adapted for attachment to the distal end of cannula housing sections 456a and 456b.

Dilator 428 includes ears 429 which extend through windows 480 formed in cannula housing sections 456a and 456b. When the surgeon desires to introduce an instrument of relatively large diameter, the surgeon may advance ears 429 and thus dilator 428 relative to cannula housing 456. Conical members 474 and gasket 472 which are positioned distal to dilator 428 are fixed with respect to cannula housing 456 and, therefore, distal movement of dilator 428 serves to dilate elements 474 and conical gasket 472.

Another seal assembly embodiment is illustrated in FIGS. 15–19. Structures which are similar to corresponding structures in the previously described seal assemblies are designated by the same reference numeral except that the lead numeral "5" replaces previous lead numbers for clarity and consistency.

Referring initially to FIGS. 15–18, seal assembly 510 includes a rigid housing 511 which defines an interior region 515 and is preferably made of ABS or polycarbonate material. Housing 511 is disposed over cannula housing 540 at one end, is capped at an opposite end by gasket 518 and end cap 507, and has a longitudinal axis, A, running between the two ends. Disposed between housing 511 and cannula housing 540 is an o-ring 598 to prevent the escape of gases and fluids from inside the body cavity through housing 511.

End cap 507 includes an aperture 505 formed therethrough and is disposed adjacent a plate member 537. Plate member 537 is mounted to end cap 507 by any suitable method, preferably a biocompatible adhesive, but alternately, may be formed integrally with end cap 507. Gasket 518 is disposed adjacent aperture 505 of end cap 507, includes an aperture 520 formed therethrough, and is at least partially received within a seal holder 582 which is preferably generally circular in shape and is disposed within annular slot 538 formed between end cap 507 and plate member 537. A flexible member 568 which preferably has a bellows construction, is also at least partially received within seal holder 582 on one side and is preferably also attached to housing 511 at the opposite side, preferably by pressure fitting the flexible member 568 between end cap 507 and plate member 537, or by any other suitable manner.

Seal assembly 510 further includes dilating member in the form of dilator 528 which is preferably made of a rigid polymeric material, e.g., ABS (acrylonitrile-butadiene-styrene) or a suitable polycarbonate material. Dilator 528 has a passageway 530 formed therein which allows for passage of instruments therethrough. Flange 532 is formed at distal end 534 of dilator 528 and is configured and dimensioned for attachment to cannula housing 540, e.g., by sonic welding, an appropriate adhesive or the like. Inner wall 533 of dilator 528 is preferably of substantially uniform diameter, whereas the outer face 535 of dilator 528 preferably includes an inwardly tapered portion 539 at its proximal end. Inwardly tapered portion 539 facilitates interaction of dilator 528 with gasket 518 when dilator 528 moves from a first position spaced from gasket 518 to a second position in contact with gasket 518 to spread aperture 520 thereof. The inner diameter of dilator 528 is selected to accommodate free passage of the instrumentation to be used therethrough and is typically on the order of 13 to 14 min. Different internal diameters may be selected, however, based on the instrumentation seal assembly 510 is intended to accommodate.

Cannula assembly 516 preferably includes a second seal member, in the form of distally directed duckbill 544 mounted between flange 532 and cannula housing 540. Duckbill 544 provides a substantially fluid-tight seal when communicating with an insufflated body cavity to substantially prevent escape of gases and fluids from inside the body cavity when no instrument is present in cannula assembly 516.

The operation of seal assembly 510 will now be described with reference to FIGS. 16–19. Prior to insertion of a surgical instruments, such as instrument 548, duckbill member 544 provides a fluid-tight seal to cannula assembly 516. Seal assembly is in a first or at-rest position with dilator 528 spaced from gasket 518, and housing 511 fully extended in the axial direction as shown in FIG. 32. In this position, seal assembly 510 can receive surgical instrumentation having a diameter which closely corresponds to the diameter of aperture 520 in gasket 518 with minimal insertion force required. Thus, if the diameter of aperture 520 is in the order of 4.5 mm, seal assembly 510 may receive surgical instruments of up to about 7 mm with minimal insertion force.

Figure 18:
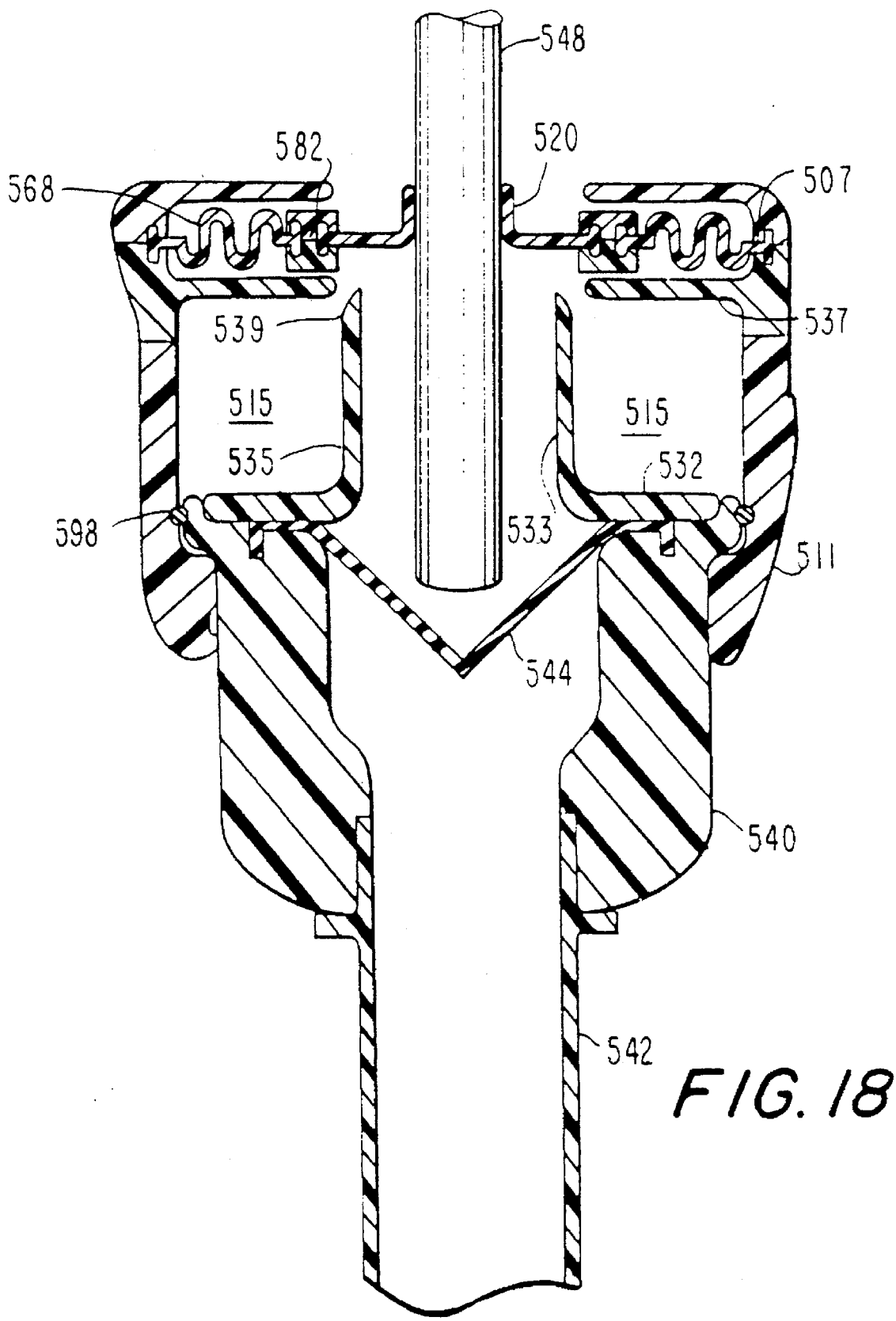
FIG. 18 is a cross-sectional view of the seal assembly of FIG. 15, which shows an instrument inserted through the seal assembly after dilation of the seal member has occured.

To insert larger diameter instruments through aperture 520, housing 511 is urged distally by the user preferably by pushing on end cap 507, thereby translating gasket 518 with respect to dilator 528. This relative translation causes gasket 518 to stretch around the inwardly tapered portion 539 of dilator 528 thereby increasing the diameter of aperture 520 as shown in FIG. 18. Instrument 548 can now be inserted through aperture 520 into passage 530 within dilator 528 and through cannula assembly 516, all with minimal insertion force.

After instrument 548 is inserted through dilator 528, housing 511 is returned to its initial position by the biasing force of gasket 518 to sealingly engages instrument 548, as shown in FIG. 18. Gasket 518 is preferably fabricated from a resilient elastomerie material, e.g., polyisoprene, which will stretch around dilator 528, but due to its resilient nature will return to its initial configuration once the user is no longer pushing on end cap 507 to stretch gasket 518. Alternately, a biasing spring may be utilized to return housing 511 to its initial position.

Figure 19:
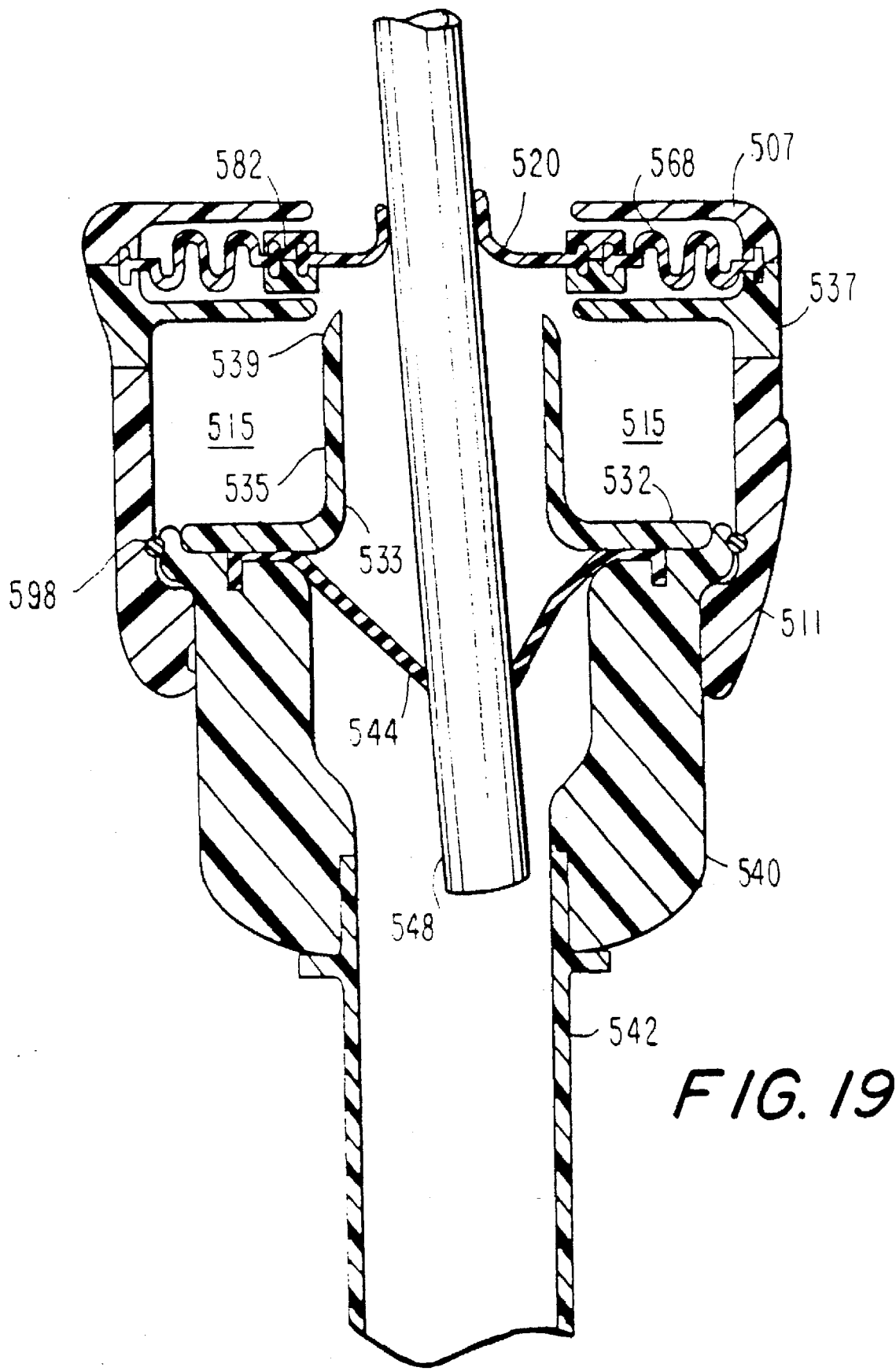
FIG. 19 is a cross-sectional view of the seal assembly of FIG. 15, which shows manipulation of an instrument inserted through the seal assembly after dilation of the seal member has occured.

Referring now to FIG. 19, after gasket 518 is returned to its initial position to sealingly engage instrument 548, instrument 548 may be manipulated within cannula assembly 516. Flexible seal 568 allows gasket 518 to remain in sealing engagement with instrument 548 by allowing gasket 548 to translate within slot 538 thereby reducing any force which would normally be applied to aperture 520 of gasket 518 through such manipulation.

If it is desired to remove instrument 548 from seal assembly 510, the user may repeat the steps described hereinabove to bring dilator 528 into engagement with gasket 518 to expand the diameter of aperture 520, thereby facilitating passage of instrument 548 with minimal force. Similarly, if it is desired to remove a specimen from within the body cavity, the user may repeat the steps described hereinabove to expand the diameter of aperture 520 to facilitate specimen passage.

An alternate seal assembly embodiment is illustrated in FIGS. 20–26. Structures which are similar to corresponding structures in the previously described seal assemblies are designated by the same reference numeral except that the lead numeral "6" has been added for clarity and consistency.

Figure 21:
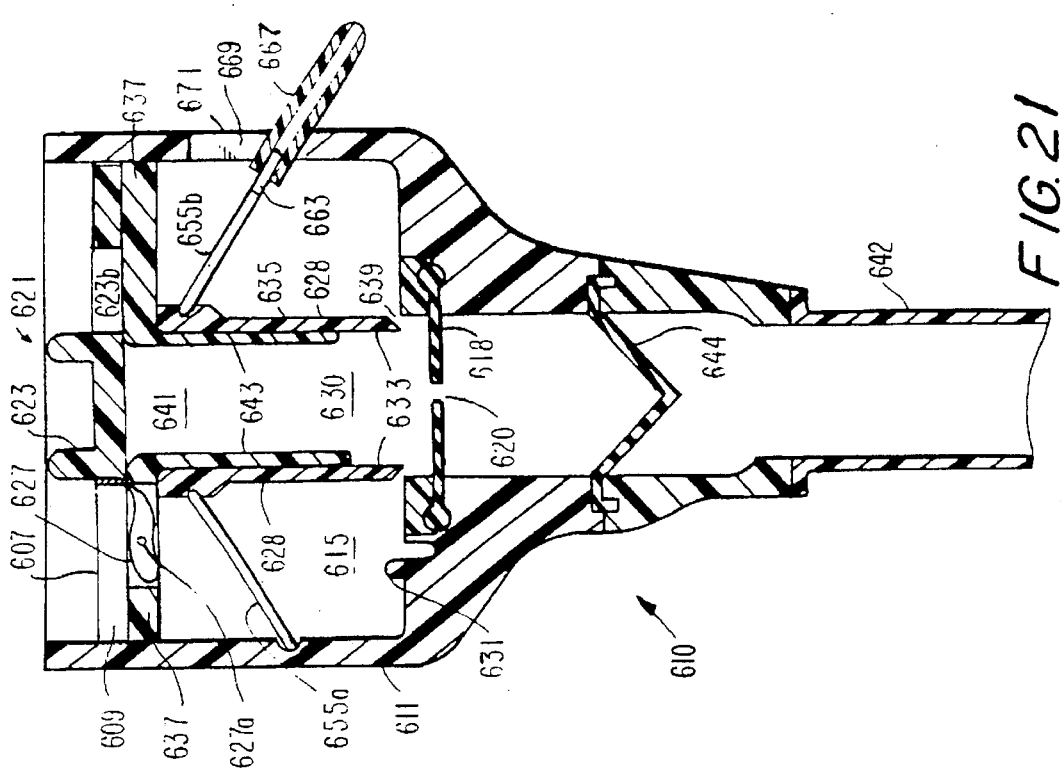
FIG. 21 is a cross-sectional view of the seal assembly illustrated in FIG. 20, which shows a seal member in a non-dilated position.
Figure 20:
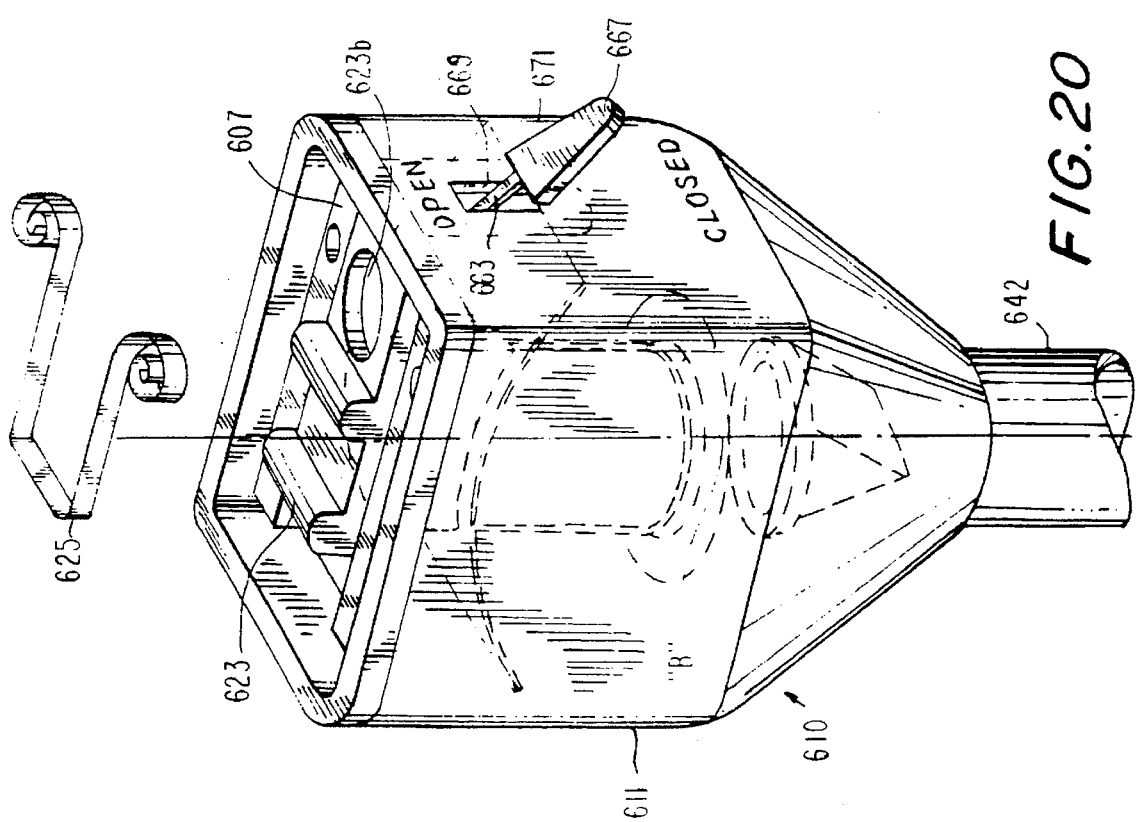
FIG. 20 is a perspective view of another seal assembly embodiment.

Referring initially to FIGS. 20–21, seal assembly 610 includes a rigid housing 611 which defines an interior region 615 and is preferably made of ABS or polycarbonate material. Housing 611 is attached at one end to a cannula 642, is capped at an opposite end by end cap 607 and sliding door 623, and has a longitudinal axis, B, running between the two ends. End cap 607 includes slot 609 disposed therein for receiving sliding door assembly 621. Door assembly 621 includes sliding door 623 which has an aperture 623b formed therethrough, a door return spring 625 which biases the sliding door 623 into a closed position, and a door latch mechanism 627 which is pivotally attached within housing 611 by pivot pin 627a for retaining the sliding door 623 in the closed position. A latch release 631 is disposed within housing 611 for releasing the door latch mechanism 627 when the sliding door 623 is moved from a first position to a second, predetermined position.

Housing 611 further includes a plate member 637 disposed therein, transverse to the longitudinal axis and in abutment with end cap 607. Plate member 637 includes an aperture 641 disposed therethrough and is positioned within a track 637a disposed in housing 611 for longitudinal movement therein. Extending longitudinally from plate member 637 is a tubular member 643. Tubular member 643 is at least partially received within a dilator 628 and is preferably formed integrally with plate member 637, but alternately, may be mounted to plate member 637 by any suitable method, e.g. a biocompatible adhesive.

Dilator 628 assumes a first position spaced from a first seal member, in the form of gasket 618, which is provided with an aperture 620 formed centrally therethrough. Dilator 628 includes a passageway 630 formed therein for allowing the passage of surgical instruments therethrough. Inner wall 633 of dilator 628 is preferably of substantially uniform diameter, whereas the outer face 635 of dilator 628 preferably includes an inwardly tapered portion 639 at its distal end. Inwardly tapered portion 639 facilitates interaction of dilator 628 with gasket 618 when dilator 628 is moved into a second position in contact with gasket 618 thereby spreading aperture 620. The inner diameter of dilator 628 is selected to accommodate the free passage of instrumentation to be used therethrough and is typically on the order of 10 to 15 min. Different internal diameters may be selected, however, based on the instrumentation seal assembly 610 is intended to accommodate.

Gasket 618 is securely affixed to the interior of housing 611 and preferably is fabricated from a resilient elastomeric material, e.g., polyisoprene. Aperture 620 of gasket 618 is preferably on the order of 4.5 mm in diameter so that it has a diameter which is less than the smallest diameter instrument which is likely to be utilized therethrough during the course of an endoscopic surgical procedure. A second seal member is also preferably provided, in the form of distally directed duckbill 644 mounted distally of gasket 618 for providing a substantially fluid-tight seal when communicating with an insufflated body cavity to substantially prevent escape of gases and fluids from inside the body cavity when no instrument is present in seal assembly 610.

Referring now to FIG. 22a, disposed circumferentially about dilator 628 is notched portion 653 which engages resilient spring members 655a and 655b which are shown disposed in a first position in FIG. 21. Resilient spring members 655a and 655b operate to bias dilator 628 into the first position spaced from gasket 618. When dilator 628 is moved into the second position contacting gasket 618 and thereby spreading aperture 620 about its inwardly tapered portion 639, resilient spring members 655a and 655b are also moved into a second position (see FIG. 20). Resilient spring members 655a and 655b, absent an external force, will return dilator 628 to the first position shown in FIG. 19.

With continuing reference to FIG. 22a, spring members 655a and 655b each have a generally rectangular body portion 657 with a generally semi-circular cutout section 659 at one end. The cutout section 659 engages notched portion 653 of dilator 628 so that longitudinal movement of dilator 628 causes corresponding movement of resilient spring members 655a and 655b, and movement of resilient spring members 655a and 655b between the first and second positions likewise results in corresponding movement of dilator 628. Either or both spring members may also have a rectangular shaped projection 663 extending from the body portion 657, opposite the cutout section 659. As best seen in FIGS. 20 and 21, rectangular projection 663 may be received within a toggle member 667 which extends from the interior region 615 of housing 611 and through a slot 669 disposed in housing wall 671 to the exterior of housing 611. Toggle member 667 enables a user to manually actuate spring members 655a and 655b between the first position where dilator 628 is spaced from gasket 618 and the second position where dilator 628 engages and spreads gasket 618.

Figure 23:
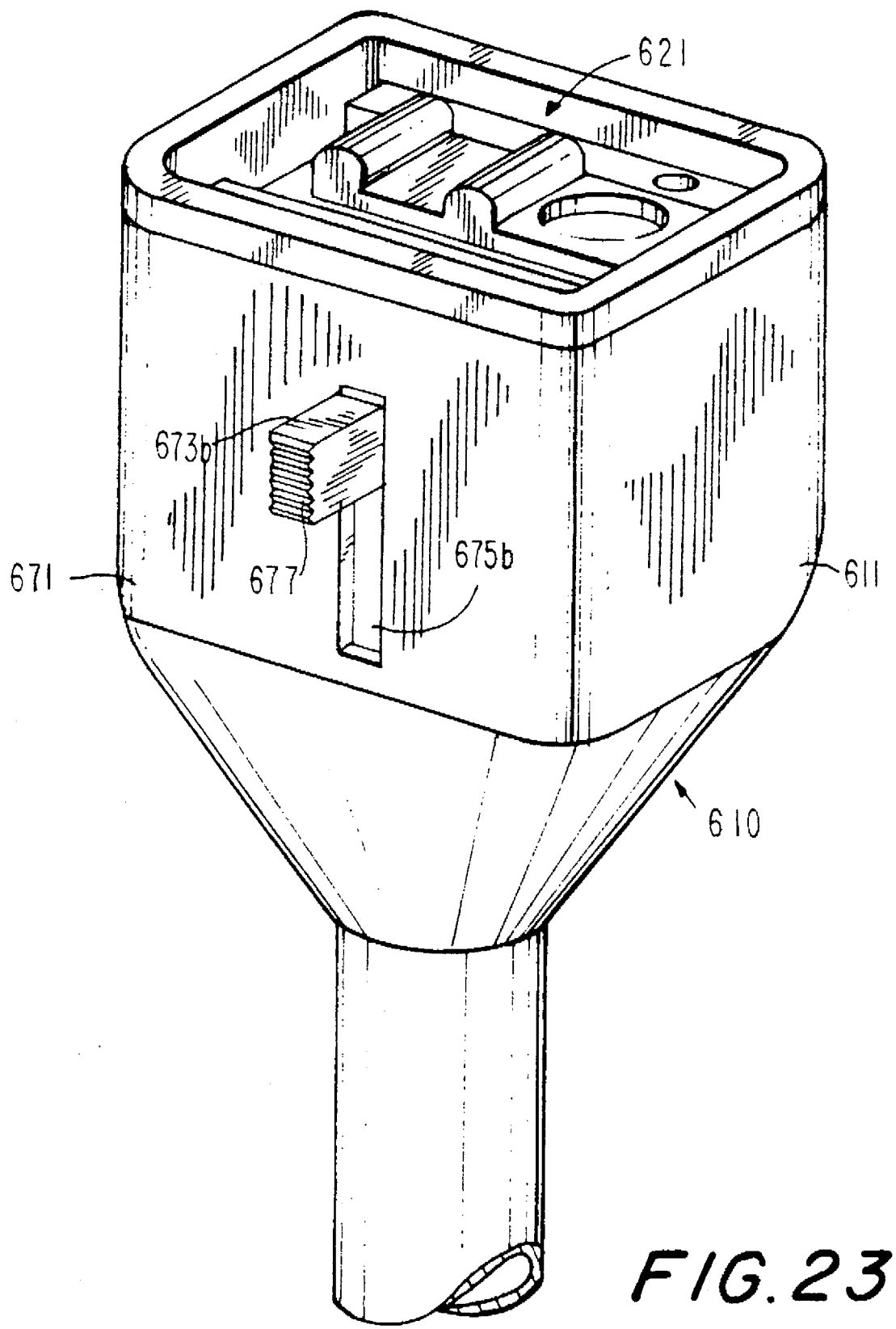
FIG. 23 is a perspective view of the seal assembly of FIG. 20 showing the alternate embodiment spring members of FIG. 22b.

In an alternate embodiment, shown in FIGS. 22b and 23, tabs 673a and 673b extend from opposite sides of the outer surface 635 of dilator 628 and through slots 675a (not shown) and 675b disposed in housing wall 671 to the exterior of housing 611. Tabs 673a and 673b each include a slot 679 disposed therethrough for receiving end portions 657a and 657b of resilient spring members 655a and 655b, respectively. Movement of tabs 673a or 673b in either a proximal or distal direction will, therefore, result in the movement of spring members 655a and 655b between the first position where dilator 628 is spaced from the gasket 618 and the second position where dilator 628 engages and spreads gasket 618. Tabs 673a and 673b also include a knurled face 677, disposed exterior housing 611, which aid the user in the gripping of tabs 673a and 673b. Tabs 673a and 673b may be formed integrally with dilator 628 or may be attached to dilator 628 by any suitable method, e.g., by a suitable adhesive.

Figure 24:
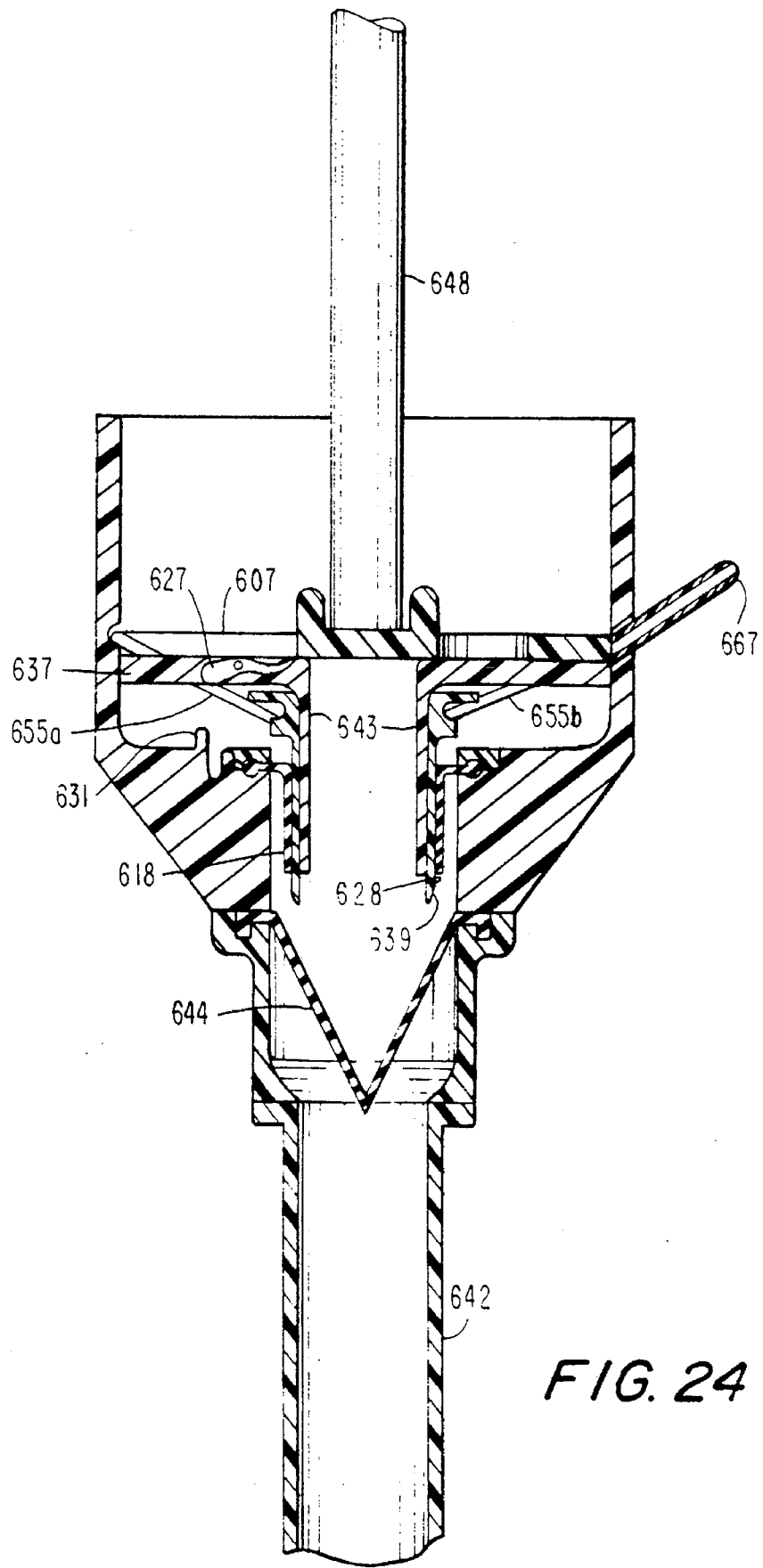
FIG. 24 is a cross-sectional view of the seal assembly of FIG. 20, which shows the end cap of the seal assembly depressed so that the dilator has moved into contact with the seal member so that the aperture of the seal member is stretched by the dilator member.

The operation of the seal assembly 610 will now be described with reference to FIGS. 21 and 24–26. Prior to the insertion of a surgical instrument, such as instrument 648, duckbill member 644 provides a fluid-tight seal between an insufflated body cavity and seal assembly 610. As shown in FIG. 24, seal assembly 610 is initially in the first, at-rest position, with dilator 628 being spaced from gasket 618 and spring members 655a and 655b biasing the dilator 628 into the first position. In this position, the sliding door 623 is retained in the closed position by door latch mechanism 627, and seal assembly 610 is therefore blocked from receiving surgical instrumentation. Retaining sliding door 623 in the closed position helps protect gasket 618 from possible damage by instrumentation which can not easily fit through gasket 618 without first spreading aperture 620, for example, a "J" hook instrument.

Figure 25:
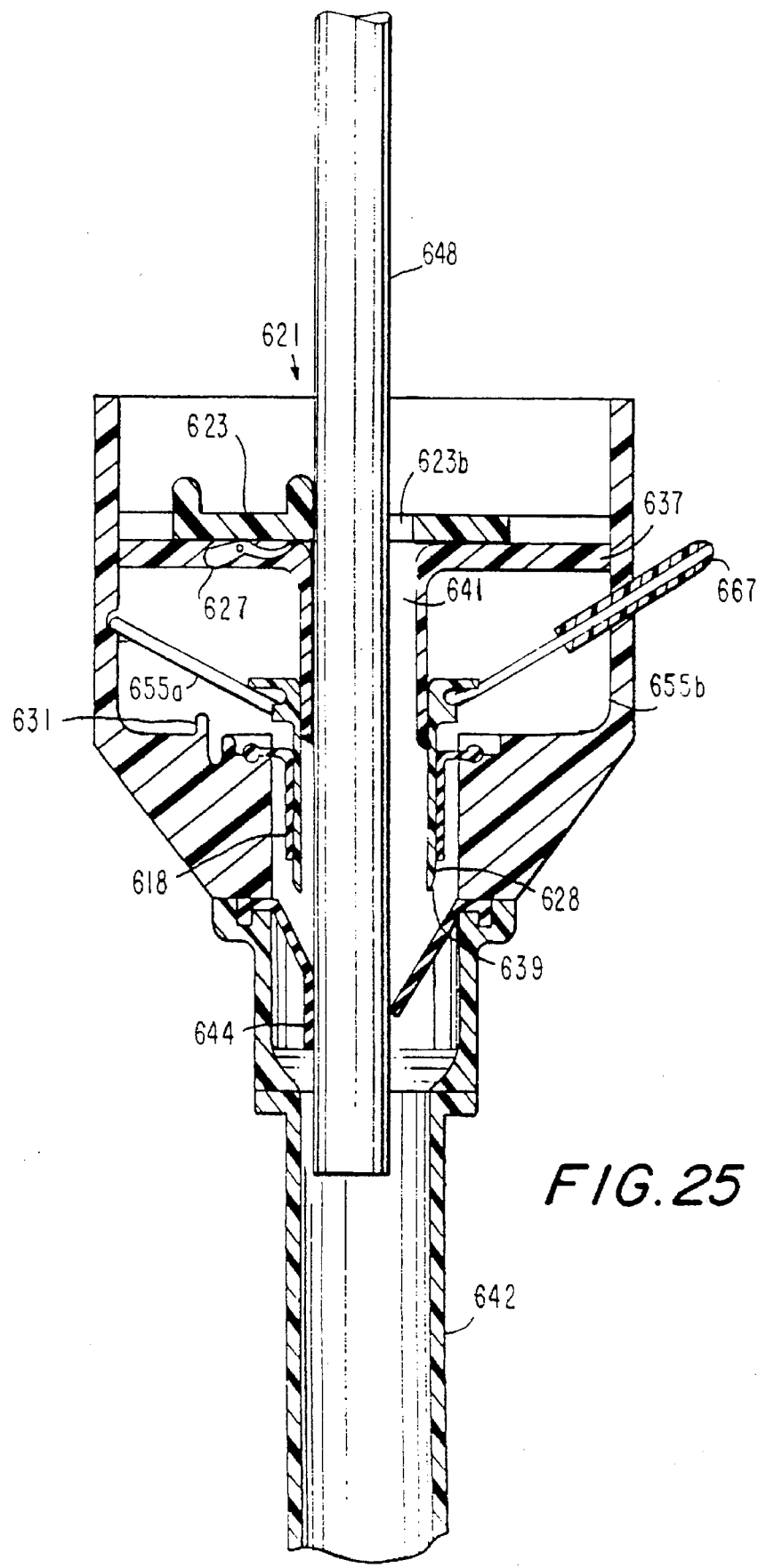
FIG. 25 is a cross-sectional view of the seal assembly of FIG. 20, which shows an instrument inserted through the seal assembly after dilation of the seal member has occured.

To permit the introduction of surgical instrumentation through aperture 620 with a minimal amount of insertion force, door assembly 621 is first urged distally by the user. The user urges the door assembly distally by pushing on it, for e.g., with instrument 648, as shown in FIG. 24. Movement of door assembly 621 distally causes corresponding movement of end cap 607 and plate member 637 which abuts end cap 607 and dilator 628. Tubular member 643 extends distally from plate member 637 and is at least partially received within dilator 628. Tubular member 643 and dilator 628 are therefore, also urged distally by the movement of door assembly 621. The relative translation of dilator 628 brings dilator 628 to the second position in contact with gasket 618 and causes aperture 620 to stretch around the inwardly tapered portion 639 of dilator 628 as shown in FIG. 20. Referring now to FIGS. 24 and 25, resilient spring members 655a and 655b, which engage dilator 628, have pivoted from their initial position biasing dilator 628 into the first position spaced from gasket 618, to their second position engaging dilator 628 with gasket 618.

Figure 26:
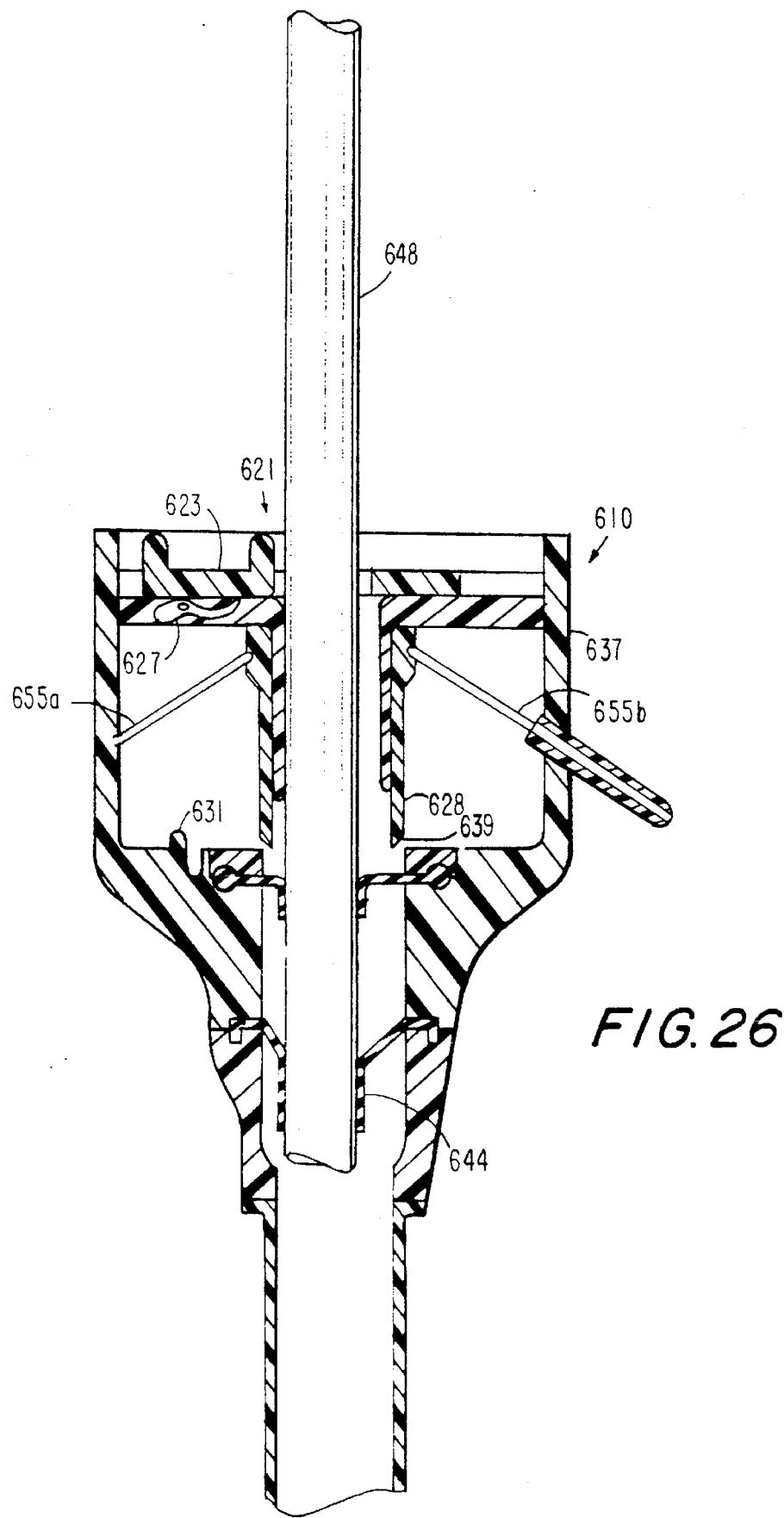
FIG. 26 is a cross-sectional view of the seal assembly of FIG. 20, which shows the instrument sealingly engaged by the seal member after dilation of the seal member has occured and the dilator has returned to its initial position.

When door assembly 621 reaches a predetermined position, latch release 631 engages door latch mechanism 627 thereby pivoting the door latch mechanism 627 and releasing sliding door 623. In this position aperture 623b of sliding door 623 is substantially aligned with aperture 641 of plate member 637. After sliding door 623 is released from engagement with door latch mechanism 627 it remains biased into the closed position by use of door return spring 625 (FIG. 20). To insert the surgical instrument 648 through seal assembly 610 the sliding door 623 must first be moved into an open position. Sliding door 623 is moved manually by pushing instrument 648 against the door 623 until it slides open. Once sliding door 623 is moved into the open position, instrument 648 can be inserted through apertures 623b and 641, into passage 630 of dilator 628 and through gasket 618 and duckbill 644 into tubular cannula 642, with minimal insertion force (FIG. 25). Referring now to FIG. 26, sliding floor 623 is now spring loaded against instrument 648 which has been inserted through gasket 618. Once the insertion of instrument 648 through dilator 628 and gasket 618 has occurred, all external force on sliding door assembly 623 is consequently removed. Thus, there no longer is an external force urging spring members 655a and 655b into the second position and as a result, both springs 655a and 655b will return to the first position, bringing dilator 628 into the first position and sealing gasket 618 about instrument 648.

If dilator 628 is returned to the first position spaced from gasket 618 and it is desired to remove instrument 648 from seal assembly 610, the user may repeat the steps described hereinabove to bring dilator 628 into engagement with gasket 618 to expand the diameter of aperture 620, thereby facilitating passage of instrument 648 with minimal force. Similarly, if it is desired to remove a specimen from within the body cavity, the user may repeat the steps described hereinabove to expand the diameter of aperture 620 to facilitate specimen passage. Alternatively, dilator 628 may be returned manually to the second position by either flipping toggle member 667 or urging tabs 673a and 673b distally. Either of these steps will urge spring members 655a and 655b into the second position along with dilator 628. If dilator 628 is moved manually, sliding door assembly 621 remains in its first position and only dilator 628 is urged distally into engagement with gasket 618.

Yet another seal assembly embodiment is illustrated in FIGS. 27–29b. Seal assembly 710 is also similar to seal assembly 610. Structures which are similar to structures in seal assembly 610 are designated with reference numerals similar to those of seal assembly 610 except a leading "7" replaces the leading "6". With the exceptions noted below, operation of seal assembly 710, as shown in FIGS. 27–29b, is essentially as described in connection with seal assembly 610 and FIGS. 20–26, hereinabove.

Figure 27:
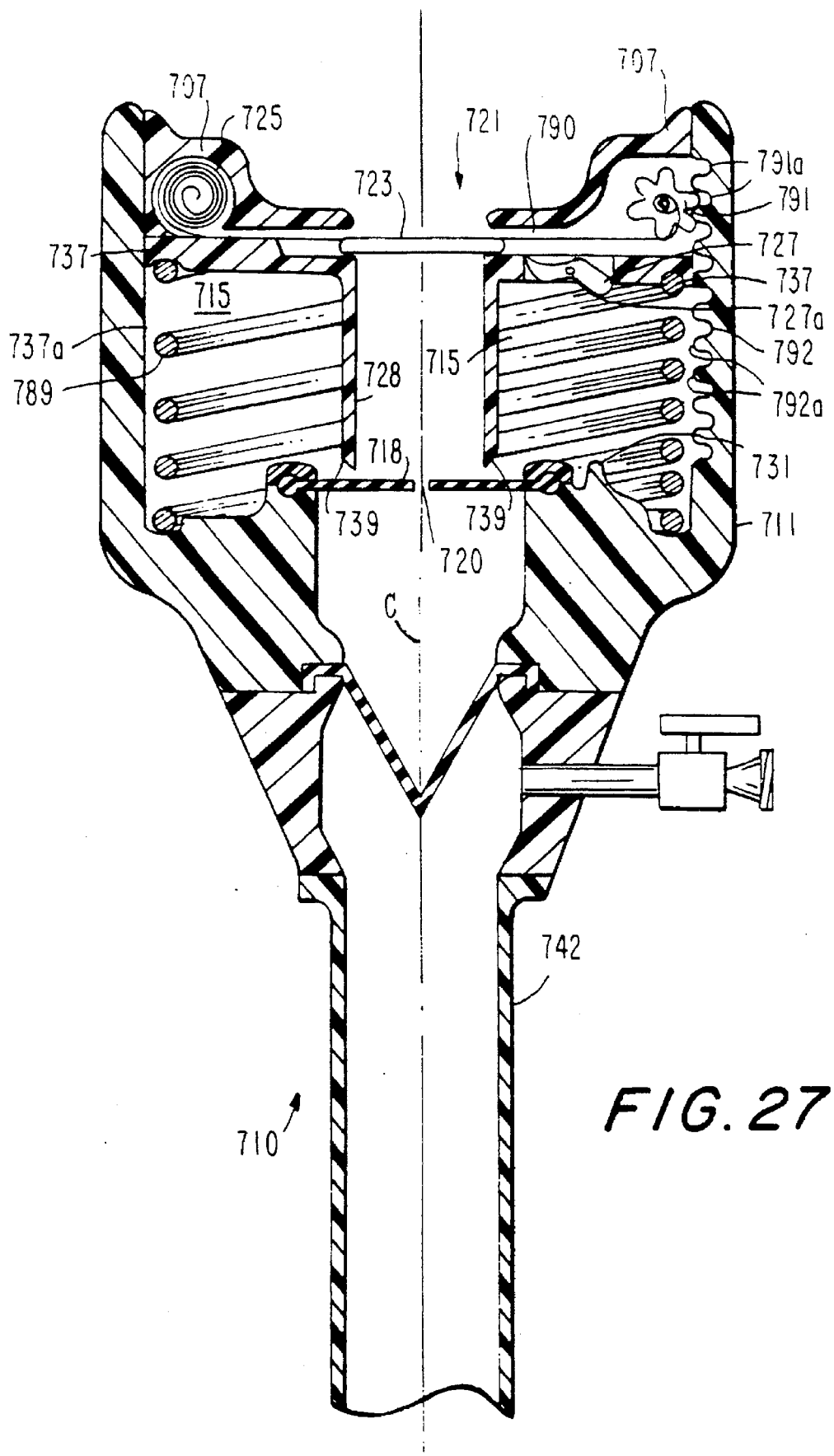
FIG. 27 is a cross-sectional view of another seal assembly embodiment.

Referring initially to FIG. 27, seal assembly 710 includes rigid housing 711 which defines an interior region 715.

Housing 711 is attached at one end to cannula 742, is capped at an opposite end by end cap 707 and sliding door 723, and has a longitudinal axis C, running between sliding door 723 and cannula 742. Sliding door 723 is part of door assembly 721 which also includes door return spring 725 for biasing sliding door 723 into a closed position and door opening spring 790 for moving sliding door 723 into an open position. Sliding door 723 is biased closed by door return spring 725 which in a first position exerts a greater force on sliding door 723 than door opening spring 790, thereby biasing sliding door 723 into the closed position and preventing the introduction of surgical instrumentation into seal assembly 710. Door latch mechanism 727, which is pivotally attached within housing 711 by pivot pin 727a, further retains sliding door 723 in the closed position.

Plate member 737 is disposed transverse to the longitudinal axis "C" and within track 737a of housing 711 for longitudinal movement therein. Plate member 737 is in abutment with end cap 707 and is integrally formed with a dilator 728 which extends longitudinally therefrom. Alternatively, dilator 728 may be mounted to plate member 737 in any suitable manner, e.g. adhesive.

Figure 28:
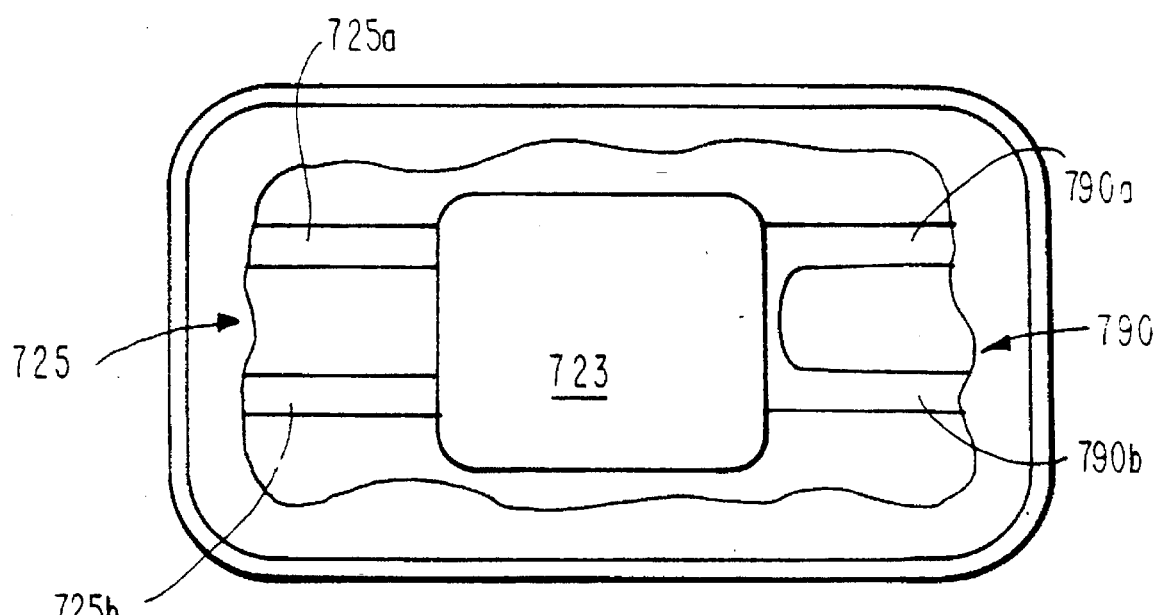
FIG. 28 is a top plan view of the seal assembly of FIG. 27 with the housing end cap partially cut away to show the sliding door and associated spring members.

As illustrated in FIG. 28, door opening spring 790 includes legs 790a and 790b and is disposed between end cap 707 and a plate member 737 which abuts end cap 707. Door opening spring 790 is preferably insert molded within sliding door 723, but may alternatively be connected to sliding door 723 in any suitable manner, for example by a biocompatible adhesive. Door return spring 725, as shown in FIG. 23, is also disposed between end cap 707 and plate member 737 and includes two springs 725a and 725b which are likewise insert molded within sliding door 723. Door return spring 725 may alternatively comprise one spring having two legs, and likewise may be attached to sliding door 723 in any suitable manner.

Referring again to FIG. 27, in order to allow the introduction of surgical instrumentation through seal assembly 710 with a minimal amount of insertion force, door latch mechanism 727 must be pivoted from engagement with sliding door 723 and the biasing force exerted by door return spring 725 on sliding door 723 must be overcome. Latch release 731, which is disposed within interior region 715 of housing 711, releases door latch mechanism 727 from engagement with sliding door 723 by contacting door latch mechanism 727 and pivoting it out of engagement with sliding door 723 when sliding door 723 is moved from a first position to a second, predetermined position. To overcome the biasing force exerted on sliding door 723 by door return spring 725, the tension exerted by door opening spring 790 on sliding door 723 must be increased until it is greater than the biasing force exerted by door return spring 725 on sliding door 723. The tension exerted by door opening spring 790 is preferably increased by use of a spring winding gear 791 which is disposed between end cap 707 and plate member 737 and is in communication with both the door opening spring 790 and a spring winding rack 792. Spring winding rack 792 extends longitudinally within the interior of housing 711 and is integrally formed therein. Spring winding rack 792 includes a plurality of teeth 792a which are dimensioned to mesh with teeth members 791a of spring winding gear 791.

Figure 29A:
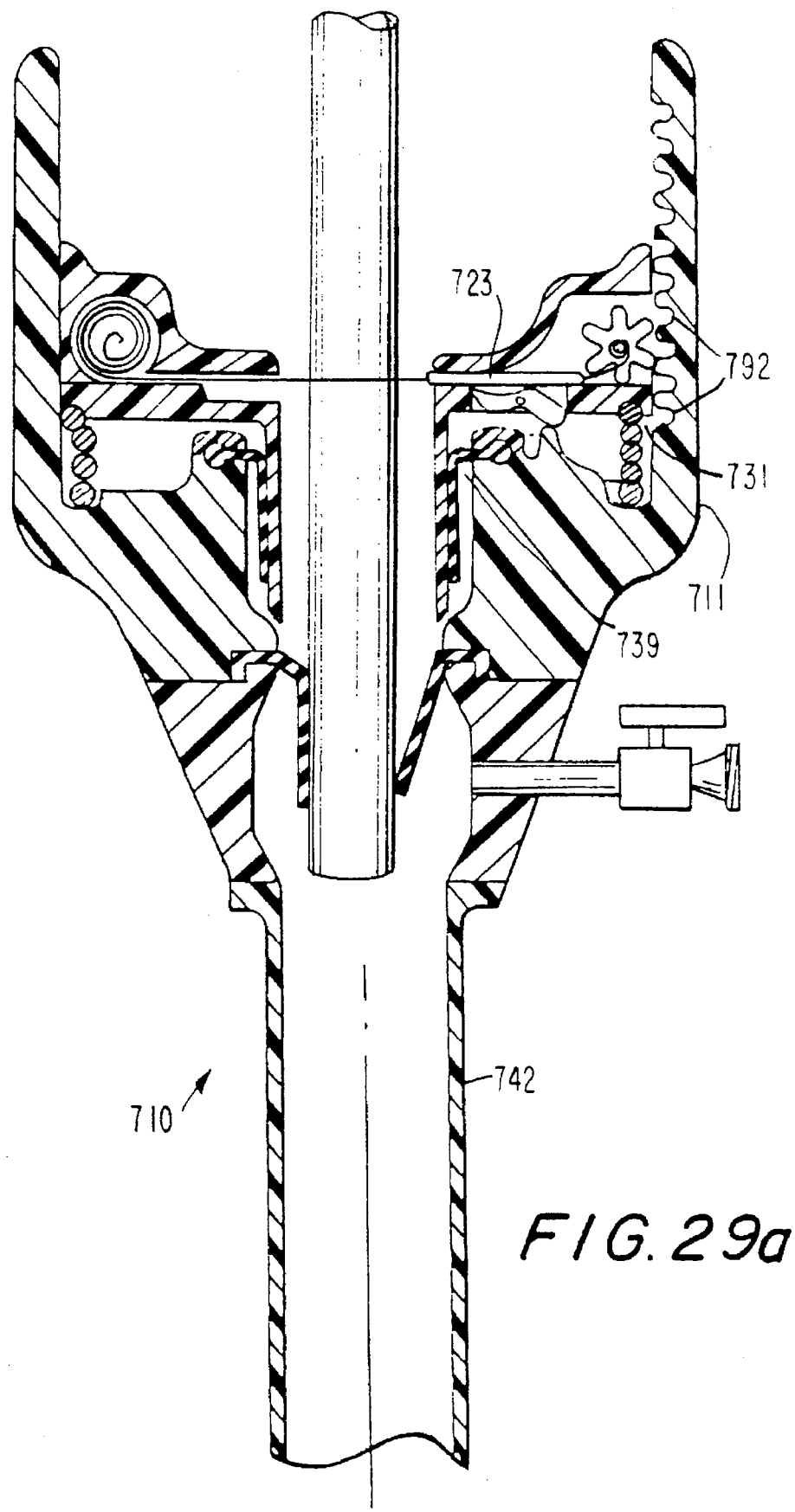
FIG. 29a is a cross-sectional view of the seal assembly of FIG. 27, which shows an instrument inserted through the seal assembly after dilation of the seal member has occured.
Figure 29B:
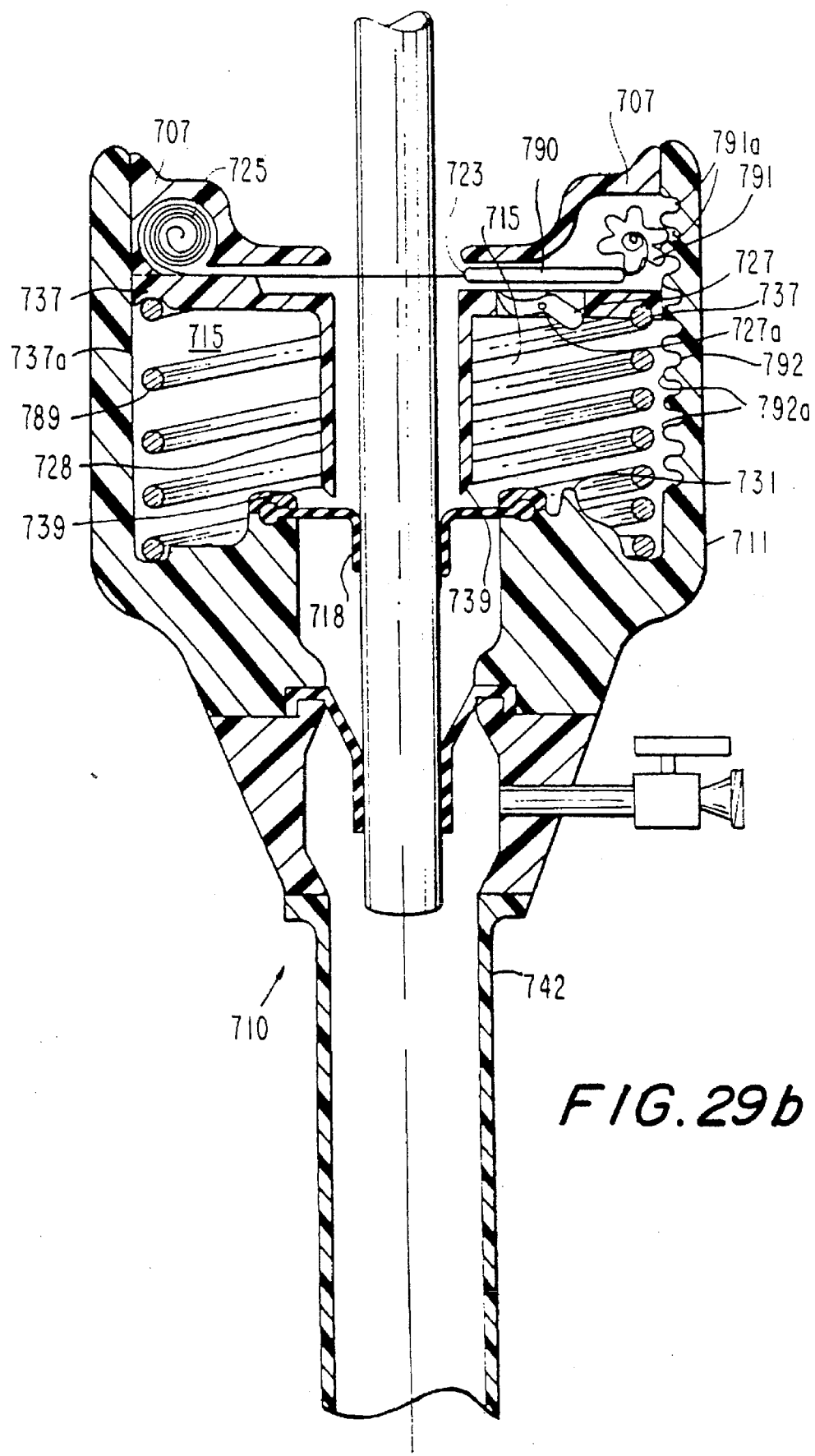
FIG. 29b is a cross-sectional view of the seal assembly of FIG. 27, which shows the instrument sealingly engaged by the seal member after dilation of the seal member has occured and the dilator has returned to its initial position.

Referring now to FIGS. 29a–29b, the operation of seal assembly 710 will now be described. To permit the introduction of surgical instrumentation through aperture 720 of gasket 718 with a minimal amount of insertion force, end cap 707 is first urged distally by the user. The user urges the end cap 707 distally by pushing on it, for e.g., with instrument 748. Movement of end cap 707 distally causes corresponding movement of sliding door 723 and plate member 737, both of which abut end cap 707. Dilator 728 extends distally from plate member 737, thus dilator 728 is also urged distally by the movement of end cap 707. The longitudinal movement of dilator 728 brings the dilator to the second position in contact with gasket 718 and causes aperture 720 to stretch around inwardly tapered portion 739 of dilator 728.

As shown in FIG. 29a, movement of sliding door 723 further produces corresponding longitudinal movement of spring winding gear 791 along spring winding rack 792. As teeth 791a of spring winding gear 791 mesh with teeth 792a of spring winding rack 792, spring winding gear 791 rotates, causing door opening spring 790 to wrap around spring winding gear 791. As door opening spring 790 wraps around spring winding gear 791 the tension exerted on sliding door 723 by door opening spring 790 is increased. At a predetermined position along spring winding rack 792, the tension exerted by the door opening spring 790 on sliding door 723 overcomes the biasing force exerted by door return spring 725 on sliding door 723, and sliding door 723 is free to open once the door latch mechanism 727 is released.

With continuing reference to FIG. 29a, the longitudinal movement of plate member 737 brings door latch mechanism 727, which is pivotally mounted to plate member 737, into engagement with latch release 731 thereby releasing door latch mechanism 727 from engagement with sliding door 723 as described hereinabove. After the user has urged sliding door 723 open, surgical instrument 748 is free to pass through dilator 728, gasket 718 and tubular cannula 742, all with minimal insertion force.

Referring now to FIG. 29b, when instrument 748 enters seal assembly 710, the force exerted on end cap 707 is removed and resilient spring member 789, which is disposed circumferentially about dilator 728 and is in abutment with plate member 737, returns dilator 728 to the first position spaced from gasket 718, thus causing gasket 718 to sealingly engage instrument 748. Sliding door 723 remains biased against instrument 748 until instrument 748 is removed. Once instrument 748 is removed from seal assembly 710, the biasing force exerted by door return spring 725 returns sliding door 723 into the closed position. Once dilator 728 is returned to its initial at-rest position and it is desired to remove instrument 748 from cannula assembly 716 and seal assembly 710, the user may repeat the steps described hereinabove to expand the diameter of aperture 720, thereby facilitating passage of instrument 748 with minimal force. Similarly, if it is desired to remove a specimen from within the body cavity, the user may repeat the steps described hereinabove to expand the diameter of aperture 720 to facilitate specimen passage.

Another seal assembly embodiment is illustrated in FIGS. 30–32b. Seal assembly 810 is similar to seal assembly 610. Structures which are similar to structures in seal assembly 610 are designated with reference numerals similar to those of seal assembly 610 except a leading "8" replaces the leading "6". With the exceptions noted below, operation of seal assembly 810, as shown in FIGS. 30–32b, is essentially as described in connection with seal assembly 610 and FIGS. 24–26, hereinabove.

Figure 30:
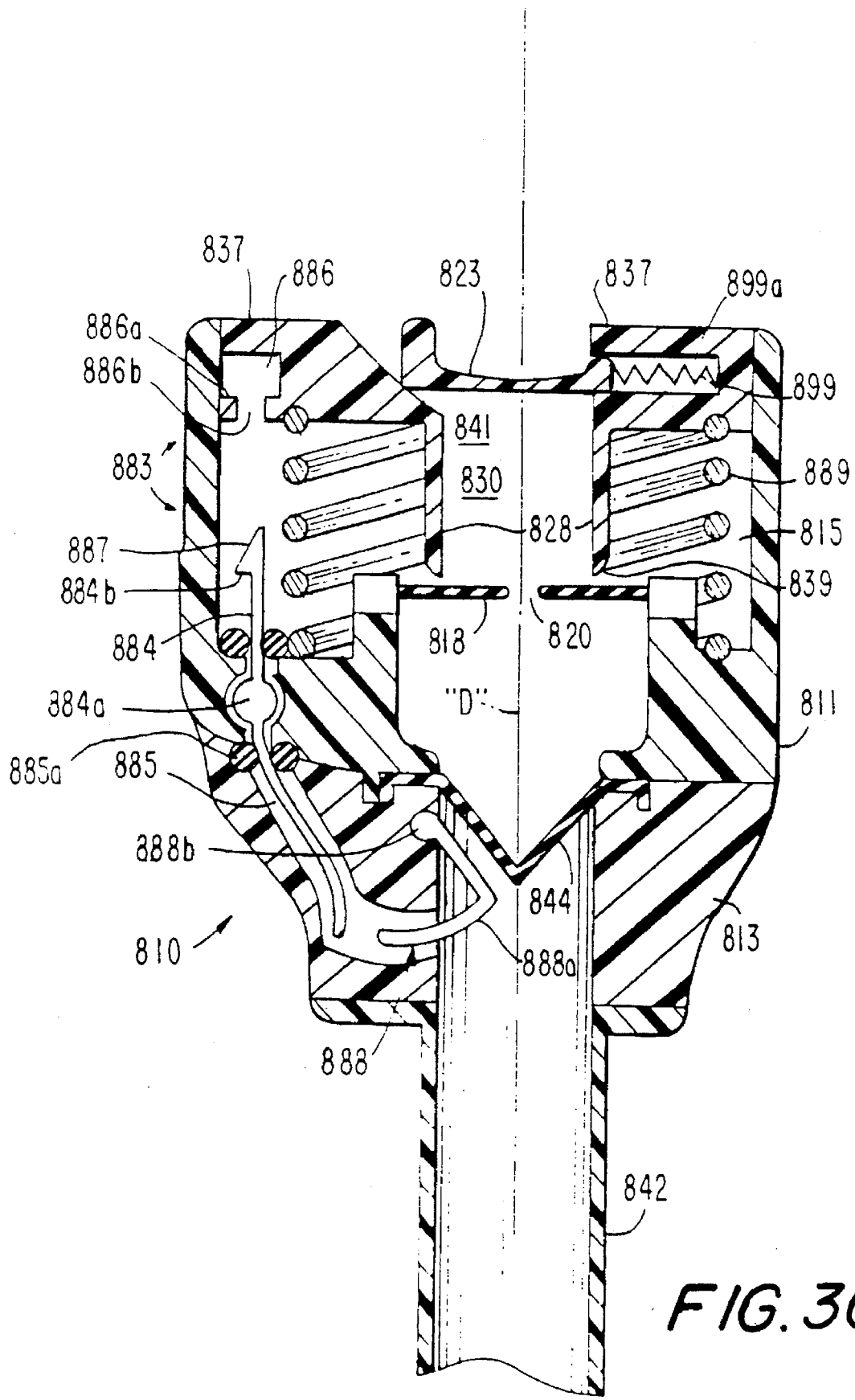
FIG. 30 is a cross-sectional view of another seal assembly embodiment.

Referring initially to FIG. 30, seal assembly 810 includes rigid housing 811 which defines an interior region 815. Housing 811 is attached at one end to cannula 842 and is capped at an opposite end by a plate member 837 and a sliding door 823, and has a longitudinal axis D running between the two ends. Sliding door 823 is biased into a closed position by door biasing spring 899 which is disposed within opening 899a of plate member 837. Plate member 837 includes an aperture 841 disposed therethrough and is positioned within a track 837a disposed in housing 811 for longitudinal movement therein. Disposed within the interior of plate member 837 is a latch receptacle 886. Latch receptacle 886 is part of seal latch mechanism 883 which further includes a latching member 884, pivotally mounted within housing 811 by pin 884a and a latch release 888, pivotally mounted within cannula housing 813, distally of duckbill seal 844. Latching member 884 is partially received within channel 885, extends into the interior region 815 of housing 811 and is in general alignment with latch receptacle 886. Latch release 888 is pivotally mounted by pin 888b, is partially received within channel 885 and includes elbow portion 888a. Channel 885 is preferably provided with a seal, such as "O-ring" 885a, to prevent the escape of gases and fluids from inside the body cavity through channel 885.

Extending longitudinally from plate member 837 is dilator 828. Dilator 828 is preferably formed integrally with plate member 837, or may alternately be mounted to plate member 837 in any suitable manner, e.g. by adhesive. Disposed circumferentially about dilator 828 and in abutment with plate member 837, is resilient spring member 889. Resilient spring member 889 biases dilator 828 into a first position spaced from a first seal member, in the form of gasket 818.

The operation of seal assembly 810 will now be described with reference to FIGS. 31–32b. To permit the introduction of surgical instrumentation through aperture 820 of gasket 818 with a minimal amount of insertion force, sliding door 823 is first urged distally by the user. The user urges the sliding door 823 distally by pushing on it, for e.g., with instrument 848. Movement of sliding door 823 distally causes corresponding movement of plate member 837 which is in engagement with sliding door 823. Dilator 828 extends distally from plate member 837, thus dilator 828 is also urged distally by the movement of sliding door 823. The longitudinal movement of dilator 828 brings the dilator to a second position in contact with gasket 818 and causes aperture 820 to stretch around inwardly tapered portion 839 of dilator 828 as shown in FIG. 31.

Figure 31:
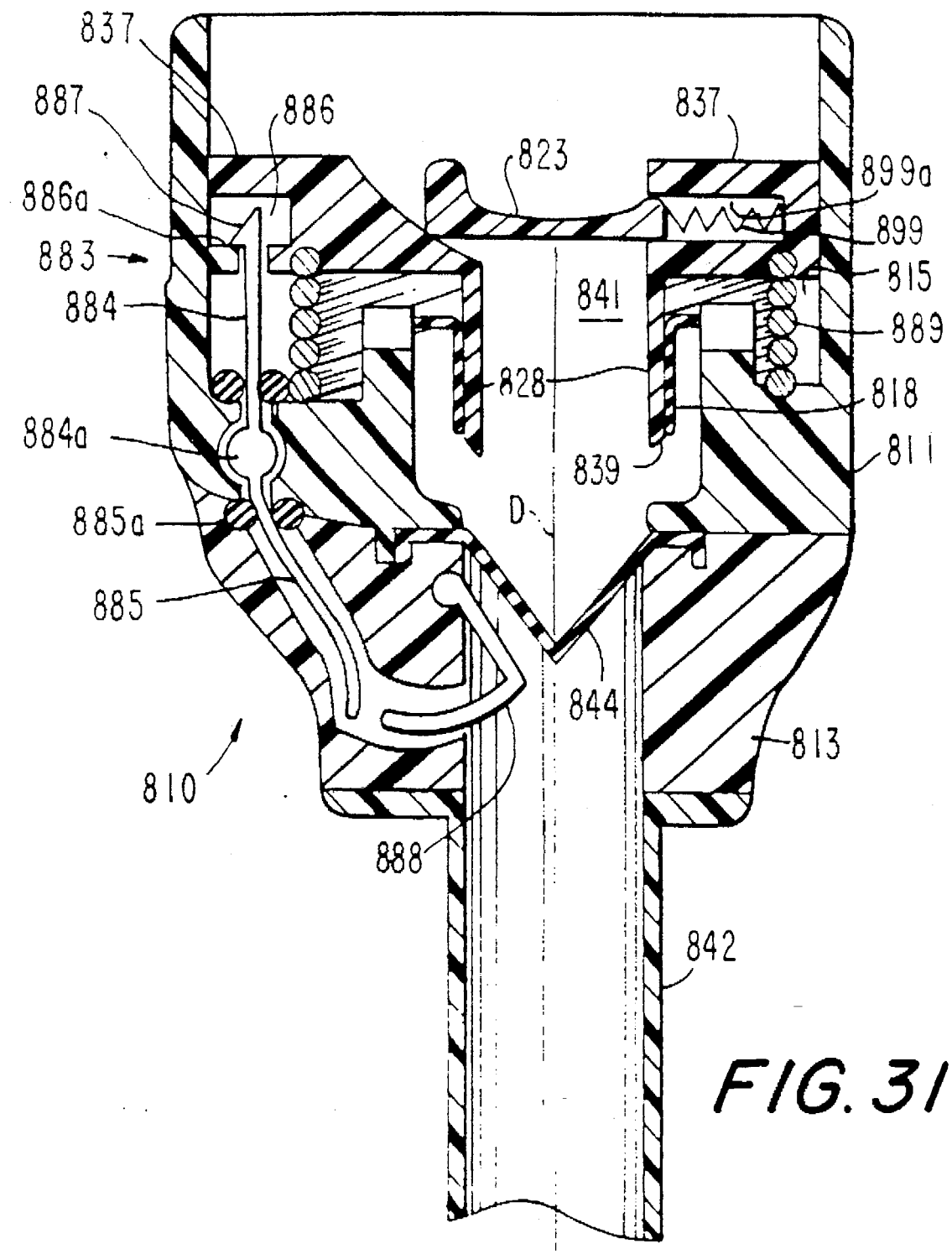
FIG. 31 is a cross-section view of the seal assembly of FIG. 30, which shows the seal member dilated and the latching member engaged within the latch receptacle.
Figure 32A:
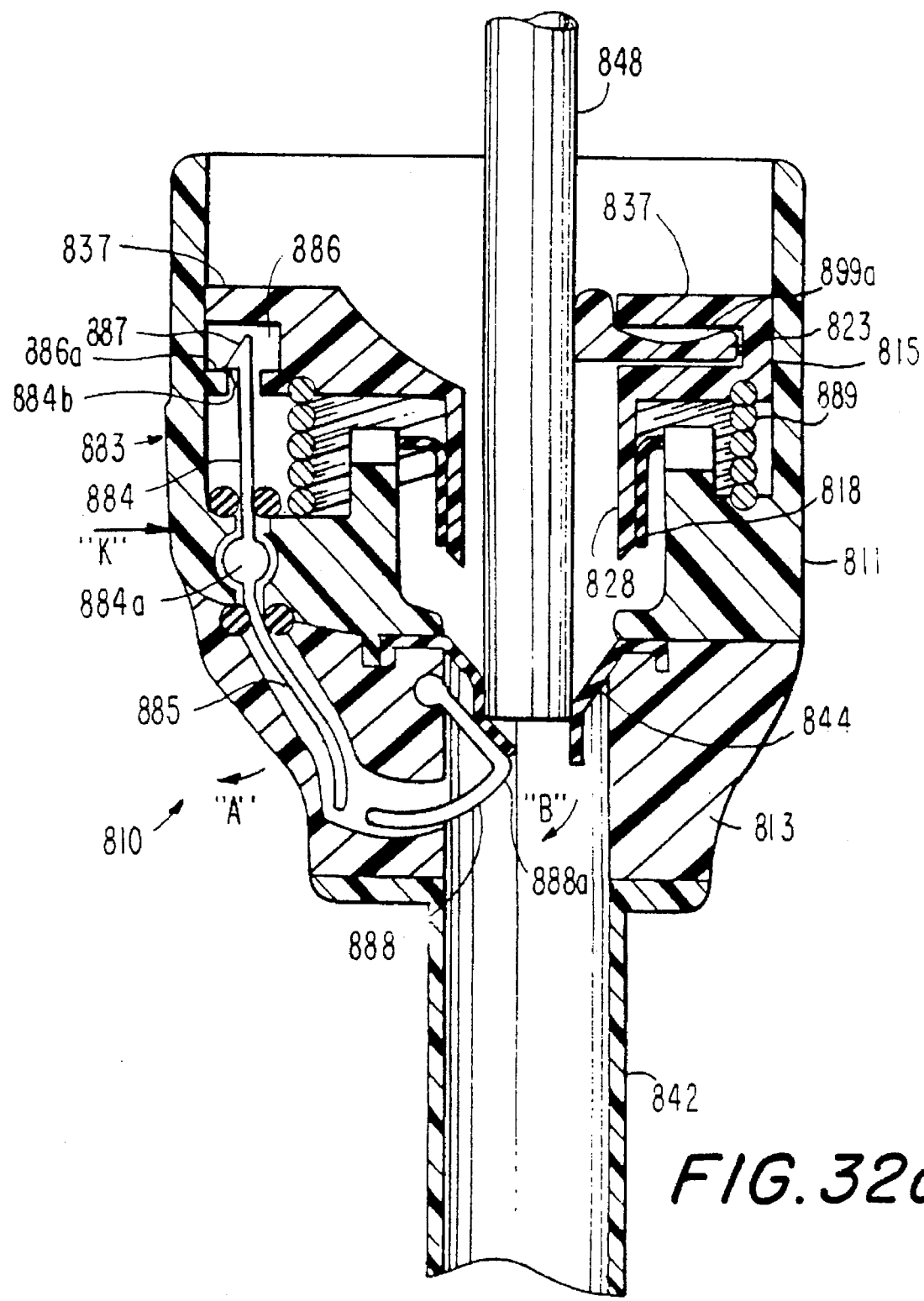
FIG. 32a is a cross-sectional view of the seal assembly of FIG. 30, showing an instrument inserted through the seal assembly after dilation of the seal member has occured, and engagement of a latch release by the instrument.

With continuing reference to FIGS. 30–31 in conjunction with FIG. 32a, as dilator 828 engages and spreads aperture 820 of gasket 818, ramped surface 887 of latching member 884 enters opening 886b of latch receptacle 886. Detent 884b of latching member 884 engages shoulder 886a of latch receptacle 886 to retain latching member 884 within latch receptacle 886. The locking of latching member 884 within latch receptacle 886 retains dilator 828 in the second position in engagement with gasket 818. After dilator 828 is retained in the second position, sliding door 823 may then be opened by pushing sliding door 823 against biasing spring 899 and into opening 899a as shown in FIG. 32a. In the embodiment of FIGS. 30–32b, however, sliding door 823 is only biased into the closed position and may, therefore, be opened at any time for reception of the surgical instrument. If the surgical instrument is of a sufficiently small diameter compared to aperture 820 when in the first position, it may not be necessary to dilate aperture 820 for insertion of the surgical instrument.

Referring now to FIG. 32a, once sliding door 823 is moved into the open position, surgical instrument 848 can be inserted through aperture 841, into passage 830 of dilator 828, through gasket 818 and duckbill 844 into cannula 842, all with minimal insertion force. As shown in FIG. 32a, when surgical instrument 848 passes through duckbill 844, it comes into contact with elbow portion 888a of latch release 888. Engagement of elbow portion 888a by a surgical instrument which has been inserted through duckbill 844 causes latch release 888 to pivot in the direction of arrow "B" thereby engaging latching member 884. Latching member 884 which is pivotally connected to housing 811, is thereby pivoted in the direction of arrow "A" at its distal end, which results in movement of its proximal end in the direction of arrow "K". Pivoting latching member 884 in the direction of arrow "K" causes detent 884b to disengage from shoulder 886a of latch receptacle 886, thereby releasing latching member 884 from within latch receptacle 886. Upon the release of latching member 884 from within latch receptacle 886, resilient spring member 889 returns dilator 828 to the first position spaced from gasket 818 to seal gasket 818 about surgical instrument 848 as shown in FIG. 32b.

Once dilator 828 is returned to its initial at-rest position and it is desired to remove instrument 848 from seal assembly 810, the user may repeat the steps described hereinabove to expand the diameter of aperture 820, thereby facilitating passage of instrument 848 with minimal force. Similarly, if it is desired to remove a specimen from within the body cavity, the user may repeat the steps described hereinabove to expand the diameter of aperture 820 to facilitate specimen passage.

Yet another seal assembly embodiment is illustrated in FIGS. 33–37. Seal assembly 910 is similar to seal assemblies 510 to 710. Structures which are similar to structures in the above seal assemblies are designated with similar reference numerals except that a leading "9" replaces any other leading number.

Figure 33:
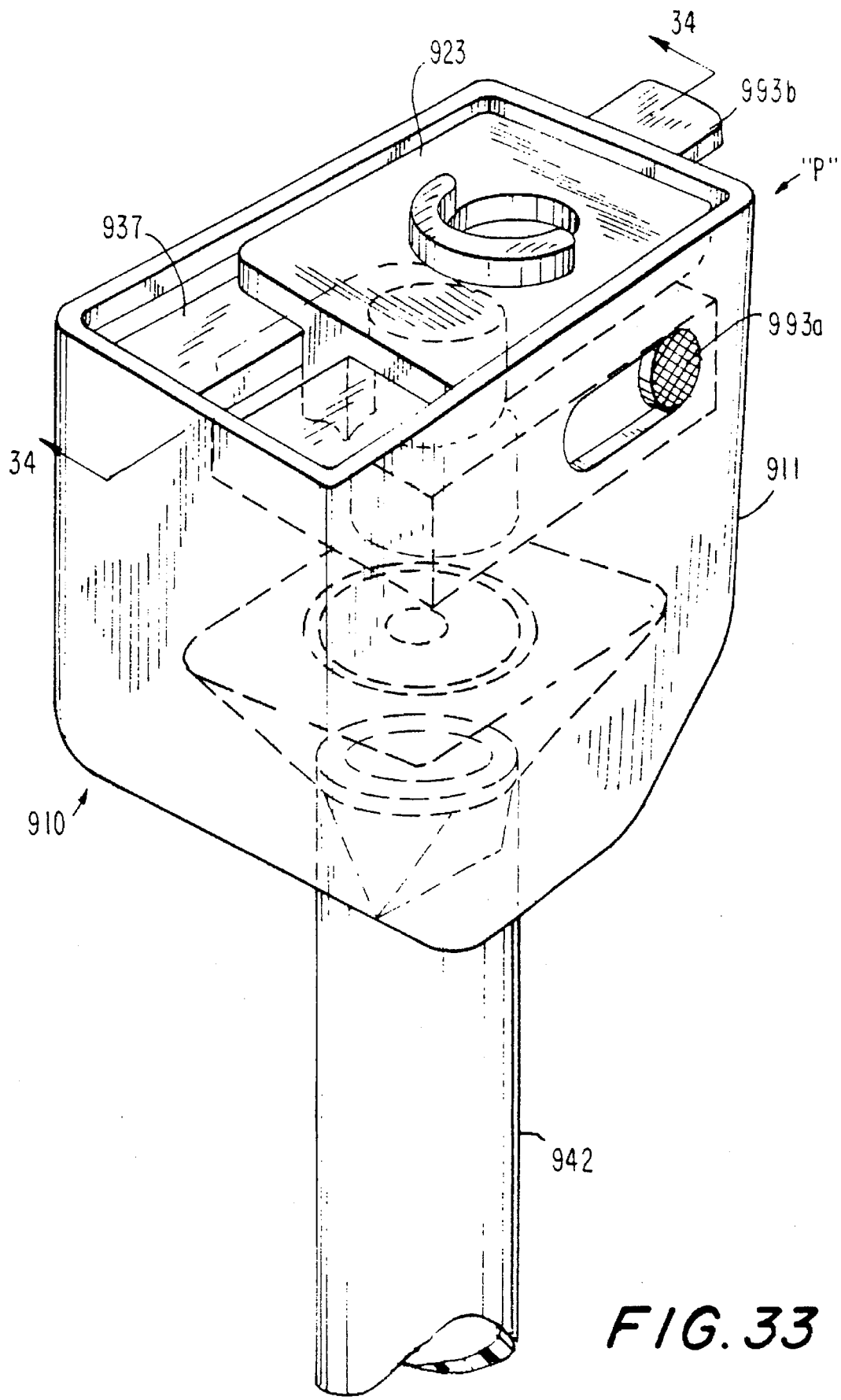
FIG. 33 is a perspective view of another seal assembly embodiment.
Figure 34:
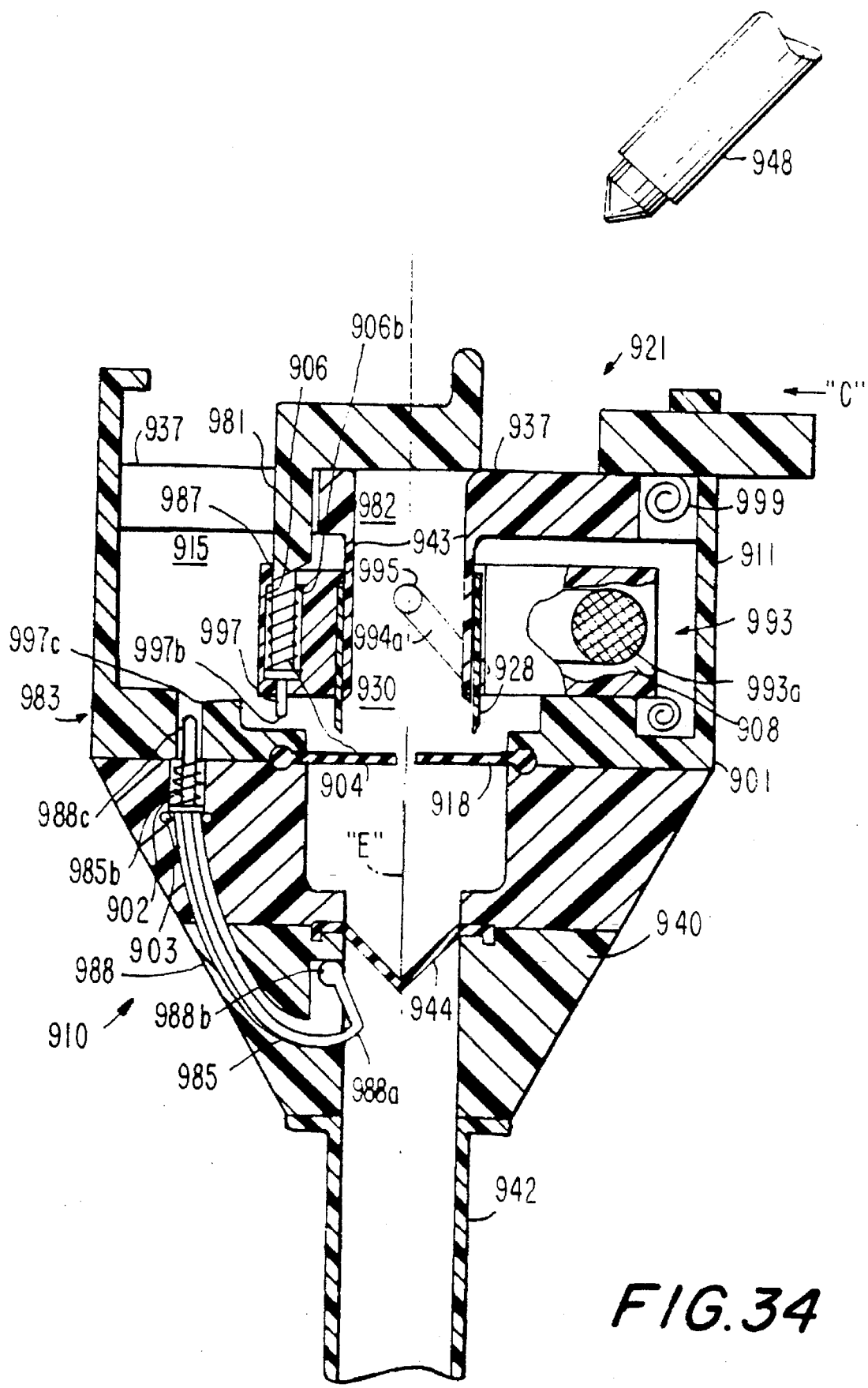
FIG. 34 is a cross-sectional view of the seal assembly illustrated in FIG. 33, which shows a seal member in a non-dilated position.

Referring initially to FIGS. 33 and 34, seal assembly 910 includes rigid housing 911 which defines interior region 915. Housing 911 is attached at one end to cannula 942, is capped at an opposite end by a sliding door 923 and plate member 937, and has a longitudinal axis E, running between the two ends. Sliding door 923 is part of door assembly 921 which also includes a door return spring 999 and a engagement member 981. Sliding door 923 is biased into a closed position by door return spring 999, thereby preventing the introduction of surgical instruments into seal assembly 910. Engagement member 981 is disposed within interior region 915 of housing 911 and includes a ramped surface 987 extending therefrom. Engagement member 981 is preferably formed integrally with sliding door 923, but alternatively may be mounted to sliding door 923 by any suitable method, e.g. adhesive.

Disposed adjacent and in abutment with sliding door 923 is plate member 937. Plate member 937 includes an aperture 941 formed therethrough and is mounted to housing 911 by any suitable method, e.g., by sonic welding, an appropriate adhesive or the like. Extending longitudinally from plate member 937 is a tubular member 943. Tubular member 943 is a least partially received within a dilator 928 and is preferably formed integrally with plate member 937, but alternately, may be mounted to plate member 937 by any suitable method, e.g. adhesive. Tubular member 943 acts to keep dilator 928 aligned with gasket 918. Dilator 928 is preferably tubular and includes a passageway 930 formed therein for receiving instruments passed therethrough. Dilator 928 is at least partially disposed within a block mechanism 993.

Referring now to FIG. 35, block mechanism 993 includes block member 908 which has cut-out ramps 994a and 994b disposed therein, and pins 995a and 995b which are slidably disposed within cut-out ramps 994a and 994b, respectively, which are in substantial alignment with respect to each other. Pins 995a and 995b are adapted to travel within ramps 994a and 994b. Dilator 928 includes apertures 996a and 996b disposed therethrough for receiving pins 995a and 995b. Therefore, movement of pins 995a and 995b within ramps 994a and 994b results in longitudinal movement of dilator 928 within block member 908. Block member 908 further includes channel 906 disposed therethrough. Channel 906 receives ramped surface 987 of engagement member 981 at one end thereof.

Referring again to FIGS. 33 and 34, housing 911 further includes seal latch mechanism 983. Seal latch mechanism 983 includes a latching pin 997 at least partially disposed within and extending from channel 906 of block member 908 and a latch release 988 which is at least partially disposed within channel 985 of housing 911. Latching pin 997 has a resilient spring member 904 circumferentially disposed thereabout which sits in shelf 906b of channel 906. Spring member 904 biases latching pin 997 into an extended position so that a first end 997b of latching pin 997 extends from channel 906 into the interior region 915 of housing 911.

Figure 37:
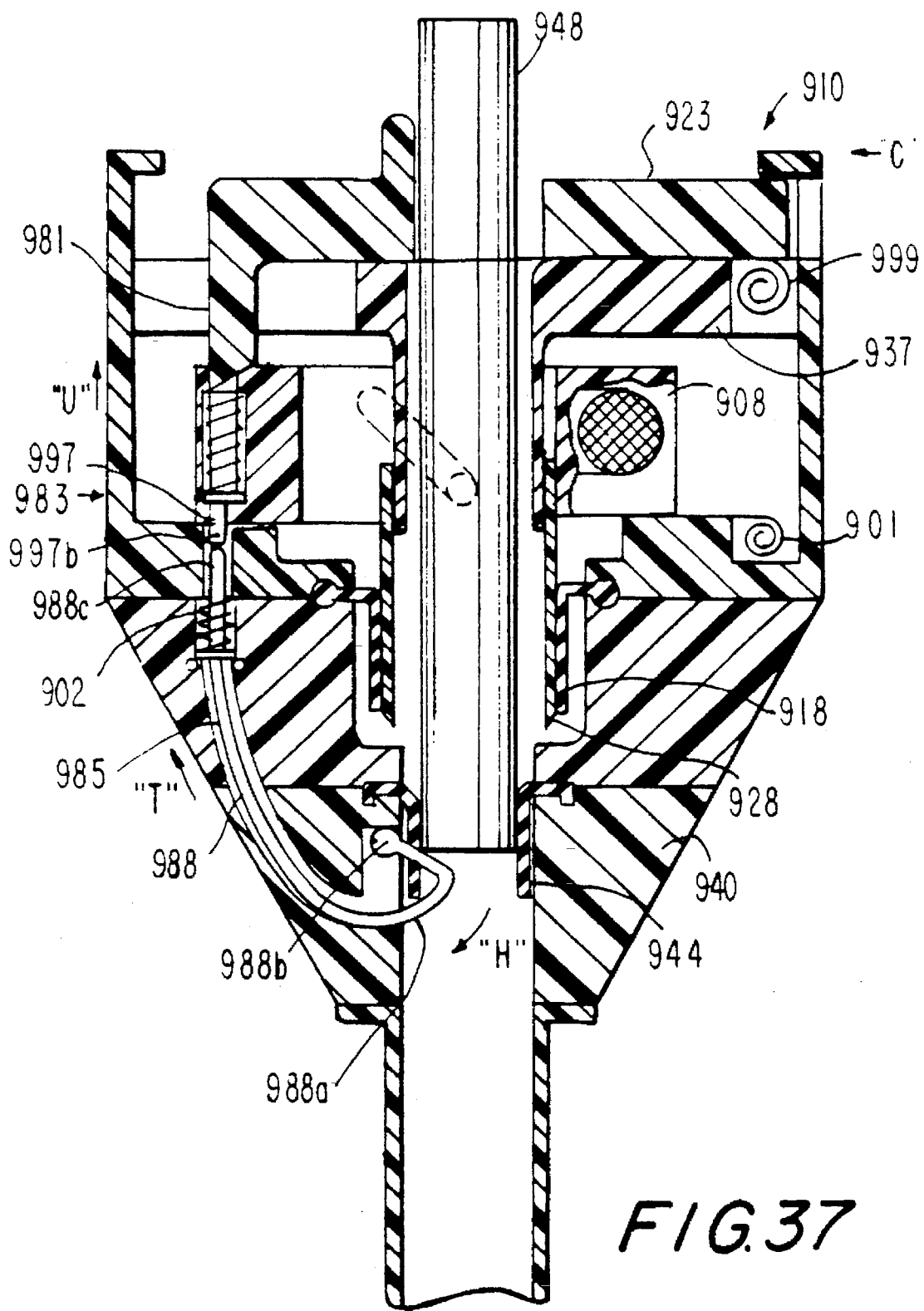
FIG. 37 is a cross-sectional view of the seal assembly of FIG. 33, showing an instrument inserted through the seal assembly after dilation of the seal member has occured, and engagement of a latch release by the instrument.

Latch release 988 is pivotally mounted by pin 988b to an interior wall of cannula housing 940 and is at least partially received within channel 985. Channel 985 is preferably provided with a seal, such as "o-ring" 903, to prevent the escape of gases and fluids from inside the body cavity through channel 985. Latch release 988 has a resilient spring member 902 circumferentially disposed about a first end 988c, the spring member being retained in shelf 985b of channel 985. Spring member 902 biases latch release 988 into an extended position so that first end 988c of latch release 988 extends from channel 985 into the interior region 915 of housing 911. Latch release 988 includes elbow portion 988a at least partially disposed within cannula 942, distally of duckbill seal 944. Engagement of elbow portion 988c by a surgical instrument which has been inserted through duckbill 944 causes elbow portion 988c to pivot in the direction of arrow "H" thereby actuating latch release 988 in the direction of arrow "T", as shown in FIG. 37.

The operation of seal assembly 910 will now be described with reference to FIGS. 34–37. Referring initially to FIG. 34, prior to the insertion of a surgical instrument, such as instrument 948, duckbill member 944 provides a fluid-tight seal between an insufflated body cavity and seal assembly 910. Seal assembly 910 is initially in the first, at-rest position, with dilator 928 being in a first position spaced from gasket 918. In this position, the sliding door 923 is retained in the closed position by door return spring 999 and seal assembly 910 is therefore blocked from receiving surgical instrument 948.

To permit the introduction of surgical instrument 948 through gasket 918 with a minimal amount of insertion force, sliding door 923 is urged in a transverse direction with respect to longitudinal axis E, represented by arrow "C" (FIG. 34) by the user. The user urges the sliding door 923 in the direction of arrow "C" by pushing on it, for e.g., with instrument 948 or by sliding button 993a or slide 993b in the direction of arrow "P" (FIG. 33). Movement of sliding door 923 causes corresponding transverse movement of engagement member 981 which is preferably formed integrally with sliding door 923. Engagement member 981 is received within channel 906 of block member 908, therefore block member 908 is also moved in the direction of arrow "C".

Referring now to FIGS. 36a–36c, as block member 908 travels in the direction of arrow "C", pins 995a and 995b (not shown) slide along ramps 994a and 994b in the direction of arrow "E". Movement of pins 995a and 995b within ramps 994a and 994b (not shown) in the direction of arrow "E" results in longitudinal movement of dilator 928 within block member 908 as represented by arrow "G" in FIGS. 36a–36c. Dilator 928 is moved longitudinally until it reaches the second position in contact with gasket 918 (FIG. 37). As dilator 928 contacts gasket 918 it causes aperture 920 to stretch about dilator 928.

Referring now to FIG. 37, as block member 908 travels in the transverse direction represented by arrow "C" (FIG. 34), latching pin 997 which is at least partially disposed within channel 906 of block member 908 is likewise moved in the transverse direction. When dilator 928 reaches the second position in contact with gasket 918, latching pin 997 travels over ramp 997c and is received within channel 985 which latches block member in the second position to maintain dilator 928 in engagement with gasket 918. v792 Surgical instrument 948 may now be inserted through seal assembly 910 and gasket 918 with minimal insertion force.

With continued reference to FIG. 37, as instrument 948 passes through duckbill 944 it contacts elbow portion 988a. Engagement of elbow portion 988a by surgical instrument 948 causes elbow portion 988a to pivot about pin 988b in the direction of arrow "H". Pivoting elbow portion 988a in the direction of arrow "H" causes latch release 988 to move in the direction of arrow "T". Since latch release 988 is in engagement with latching pin 997, latching pin 997 also moves in the direction of arrow "T". Movement of latching pin 997 in the direction of arrow "T" releases latching pin 997 from channel 985.

With continuing reference to FIG. 37, latching pin 997 is in abutment with engagement member 981, therefore movement of latching pin 997 in the direction of arrow "T" results in corresponding movement of engagement member 981 in the direction of arrow "U". As engagement member 981 is moved in the direction of arrow "U" it disengages from channel 906 of block member 908. Releasing latching pin 997 from channel 985 and disengaging engagement member 981 from block member 908 results in block mechanism 993 being returned to the first position by the force of a biasing return spring 901 which is disposed within housing 911 and is attached to block member 908.

Returning block mechanism 993 to the first position causes pin 995 to travel back to its original position, thereby resulting in the movement of dilator 928 to the first position spaced from gasket 918, thereby sealing gasket 918 about the surgical instrument 948 inserted therethrough. Although block mechanism 993 returns to the first position, sliding door 923 remains biased against the surgical instrument 948 and does not return to the first position as engagement member 981 which is preferably formed integrally with sliding door 923 has been disengaged from block member 908. Upon removal of the surgical instrument from seal assembly 910, sliding door 923 and hence engagement member 981, are both returned to the first position by the force of door return spring 999. Ramped surface 987 of engagement member 981 will then contact and enter channel 906 of block member 906 to re-engage engagement member 981 with block member 908.

It will be understood that various modifications may be made to the embodiments disclosed herein. For example, the seal dilator may be positioned such that the dilator is movable instead of the sealing gasket or vice versa. Also, the various seal assemblies may either be formed integrally with a cannula and cannula assembly or may be detachably mounted thereto. In addition, any of the embodiments may benefit from the flexible member shown in FIG. 16. Therefore, the above description should not be construed as limiting, but merely as exemplifications of preferred embodiments. Those skilled in the art will envision other modifications within the scope and spirit of the claims appended hereto.

What is claimed is:

1. A seal assembly which comprises:
   (a) a unitary housing defining a cavity therein;
   (b) a deformable gasket positioned within the housing and defining an aperture to receive surgical instrumentation;
   (c) a dilating member positioned at least partially within the housing cavity in coaxial alignment with the deformable gasket for movement between a first position adjacent the gasket and a second position in engagement with the gasket whereby the aperture is expanded; and
   (d) a biasing mechanism mounted in the housing cavity and accessible through the housing, the biasing mechanism being positioned to urge the dilating member to the first position.

2. In combination:
   (a) an elongated cannula having proximal and distal ends and a throughbore; and
   (b) a sealing mechanism operably associated with the proximal end of the cannula, the sealing mechanism including:
      (i) housing;
      (ii) deformable sealing member having a body with a passage formed through the body;
      (iii) a dilator member supported within the sealing mechanism housing, the dilator member having a central bore having a diameter substantially equal to the diameter of the cannula throughbore, the dilator member being movable from a first position in which the sealing member is in a predeformed position to a second position in which the sealing member is deformed to increase the area of the sealing member passage.

3. A cannula assembly which comprises:
   (a) a housing;
   (b) a resilient first gasket disposed within the housing, wherein the first gasket includes an aperture formed therein to receive surgical instrumentation;
   (c) a biasing mechanism positioned within the housing;
   (d) a cannula having a throughbore operatively associated with the housing;
   (e) a dilating member having an exterior face associated with the housing and having a bore with a diameter substantially the same as the diameter of the cannula throughbore;
   wherein the first gasket and the dilating member are adapted for relative movement therebetween, the dilating member assuming a first position spaced from the first gasket, and assuming a second position wherein the aperture of the first gasket is stretched around the exterior face of the dilating member to allow free passage of surgical instrumentation of varying diameter with minimal insertion force into the cannula, the biasing mechanism returning the dilating member to the first position spaced from the first gasket after insertion of the instrument thereby allowing the first gasket to sealingly engage the surgical instrumentation.

4. The seal assembly of claim 3, wherein the first gasket is substantially planar and is mounted transverse with respect to the housing.

5. The seal assembly of claim 1, wherein the housing includes a seal mechanism, the seal mechanism being configured and dimensioned to provide a substantially fluid-tight seal in the absence of an instrument passing therethrough.

6. The seal assembly of claim 5, wherein the seal mechanism comprises a distally directed duckbill member.

7. The seal assembly of claim 5 further comprising a latching mechanism disposed within the housing for retaining the dilating member in the second position.

8. The seal assembly of claim 1, wherein the biasing mechanism comprises at least one spring member.

9. The seal assembly of claim 8, wherein the at least one spring member comprises a circumferential resilient spring disposed about the dilating member.

10. The seal assembly of claim 8, wherein the at least one spring member comprises at least one substantially planar, flexible spring member positioned to act upon the dilating member.

11. The seal assembly of claim 1 further comprising an actuating mechanism in communication with the dilating member, for moving the dilating member between the first position and the second position.

12. The seal assembly of claim 11 wherein the actuating mechanism is manually actuable.

13. The seal assembly of claim 1 further comprising a door assembly transverse the housing, wherein longitudinal movement of the door assembly from a rest position to a predetermined displaced position results in corresponding movement of the dilating member from the first position to the second position.

14. The seal assembly of claim 13 wherein the door assembly comprises a slidable door, slidable between a first, closed position and a second, opened position.

15. The seal assembly of claim 14 wherein the door assembly comprises a door return spring for biasing the door to the first, closed position.

16. The door assembly of claim 15 further comprising a door opening spring in communication with a spring winding gear for winding the door opening spring.

17. The seal assembly of claim 16 wherein the door return spring maintains a greater tensile force on the door than the door opening spring when the door assembly is at the proximal position, the greater tensile force maintaining the door in the first, closed position.

18. The seal assembly of claim 16 further comprising a spring winding rack disposed within the housing and in communication with the spring winding gear.

19. The seal assembly of claim 18 wherein the spring winding rack is longitudinally disposed within the housing.

20. The seal assembly of claim 18 wherein the spring winding rack and the spring winding gear are a rack and pinion assembly.

21. The seal assembly of claim 18 wherein longitudinal movement of the door assembly from the proximal position to the distal position results in rotational movement of the spring winding gear, distally along the spring winding rack, thereby causing corresponding movement of the door opening spring about the spring winding gear resulting in increased tensile force on the door by the door opening spring wherein the increased tensile force causes the door to open when the spring reaches the distal position.

22. The seal assembly of claim 15 further comprising a door latch mechanism pivotally disposed within the housing, adjacent the door, for maintaining the door in the first, closed position.

23. The seal assembly of claim 22 further comprising a latch release disposed distally within the housing, wherein movement of the door from the rest position to the predetermined displaced position causes the latch release to engage the door latch mechanism thereby disengaging the latch mechanism and releasing the door.

24. The seal assembly of claim 3 comprising a block assembly disposed about the dilating member, said block assembly comprises a cut-out ramp having a pin slidably disposed therethrough, the pin operatively communicating with the dilating member, wherein movement of the block assembly causes the pin to move within the cut-out ramp thereby causing the dilating member to move from the first position to the second position.

25. The seal assembly of claim 24, wherein the housing includes a seal mechanism, the seal mechanism being configured and dimensioned to provide a substantially fluid-tight seal in the absence of an instrument passing therethrough.

26. The seal assembly of claim 25 further comprising a latching mechanism disposed within the housing for retaining the dilating member in the second position.

27. The seal assembly of claim 26 further comprising a latch release mechanism disposed within the housing, distal the first gasket, wherein actuation of the release mechanism releases the latching mechanism thereby allowing the dilating member to return to the first position.

28. The seal assembly of claim 27 wherein the release mechanism is disposed distally of the seal mechanism.

* * * * *